(12) United States Patent
Dhilawala et al.

(10) Patent No.: US 11,238,980 B2
(45) Date of Patent: Feb. 1, 2022

(54) SYSTEMS AND METHODS TO AUTOMATE TRANSFER, STORAGE, AND ANALYSIS OF MEDICAL DEVICE DATA

(71) Applicant: Galen Data, Inc., Houston, TX (US)

(72) Inventors: Abbasi N. Dhilawala, Houston, TX (US); Christopher G. Dupont, League City, TX (US)

(73) Assignee: GALEN DATA, INC., Houston, TX (US)

( * ) Notice: Subject to any disclaimer, the term of this patent is extended or adjusted under 35 U.S.C. 154(b) by 390 days.

(21) Appl. No.: 15/934,025

(22) Filed: Mar. 23, 2018

(65) Prior Publication Data

US 2018/0294057 A1    Oct. 11, 2018

Related U.S. Application Data

(60) Provisional application No. 62/476,632, filed on Mar. 24, 2017.

(51) Int. Cl.

| | |
|---|---|
| *G16H 40/60* | (2018.01) |
| *G16H 10/60* | (2018.01) |
| *G16H 40/20* | (2018.01) |
| *G16H 80/00* | (2018.01) |
| *G16H 30/00* | (2018.01) |
| *G16H 15/00* | (2018.01) |

(52) U.S. Cl.
CPC ............ *G16H 40/60* (2018.01); *G16H 10/60* (2018.01); *G16H 40/20* (2018.01); *G16H 15/00* (2018.01); *G16H 30/00* (2018.01); *G16H 80/00* (2018.01)

(58) Field of Classification Search
CPC ........ G16H 40/60; G16H 40/20; G16H 10/60; G16H 15/00; G16H 30/00; G16H 80/00

USPC ............................................................ 705/2
See application file for complete search history.

(56) References Cited

U.S. PATENT DOCUMENTS

| | | |
|---|---|---|
| 7,337,407 B1 | 2/2008 | Ogami et al. |
| 9,372,688 B1 | 6/2016 | Ben-Yair et al. |
| 9,460,077 B1 * | 10/2016 | Casey ................ G06F 16/2365 |

(Continued)

FOREIGN PATENT DOCUMENTS

| | | | |
|---|---|---|---|
| EP | 2177986 A1 * | 4/2010 | ............... G06F 8/20 |
| WO | 2018175944 | 9/2018 | |

OTHER PUBLICATIONS

Williams, P. A., & Woodward, A. J. (2015). Cybersecurity vulnerabilities in medical devices: a complex environment and multifaceted problem. Medical devices (Auckland, N.Z.), 8, 305-316. doi:10.2147/MDER.S50048. (Year: 2015).*

(Continued)

*Primary Examiner* — Joshua B Blanchette
*Assistant Examiner* — Winston Furtado
(74) *Attorney, Agent, or Firm* — Williams Morgan, P.C.

(57) ABSTRACT

Systems and methods for automated generation of medical device communication software, cloud-based storage of medical device data including an electronic medical device (EMD) application communication interface and a central communication interface, and user interface software to allow a user device to receive EMD data transmitted from a data storage medium (DSM) and transmit data to the DSM for transmission to the EMD, that meets one or more medical device standards set by government or industry regulatory bodies.

25 Claims, 9 Drawing Sheets

(56) References Cited

U.S. PATENT DOCUMENTS

| | | | |
|---|---|---|---|
| 9,766,955 B2 | 9/2017 | Ahmed et al. | |
| 2002/0002326 A1* | 1/2002 | Causey, III | A61B 5/0002 |
| | | | 600/300 |
| 2003/0004971 A1 | 1/2003 | Gong et al. | |
| 2003/0225935 A1* | 12/2003 | Rivard | G06F 8/51 |
| | | | 719/328 |
| 2004/0148586 A1* | 7/2004 | Gilboa | G06F 3/0484 |
| | | | 717/108 |
| 2005/0055242 A1* | 3/2005 | Bello | G06Q 50/22 |
| | | | 705/2 |
| 2005/0261934 A1* | 11/2005 | Thompson | G16H 40/67 |
| | | | 705/2 |
| 2006/0031094 A1* | 2/2006 | Cohen | G16H 20/10 |
| | | | 705/2 |
| 2009/0031230 A1 | 1/2009 | Kesler | |
| 2010/0292556 A1* | 11/2010 | Golden | G16H 40/67 |
| | | | 600/364 |
| 2011/0145784 A1* | 6/2011 | Zhao | G06F 30/30 |
| | | | 717/106 |
| 2013/0024843 A1 | 1/2013 | Kutlu | |
| 2013/0124616 A1 | 5/2013 | Bullotta et al. | |
| 2013/0241306 A1* | 9/2013 | Aber | H02J 7/342 |
| | | | 307/104 |
| 2015/0066538 A1* | 3/2015 | Dantsker | G06F 19/3418 |
| | | | 705/3 |
| 2016/0029420 A1* | 1/2016 | Rajan | A61B 5/0008 |
| | | | 370/329 |

OTHER PUBLICATIONS

Lepmets, M., Clarke, P., McCaffery, F., Finnegan, A., & Dorling, A. (2015). Development of MDevSPICE®—the medical device software process assessment framework. Journal of Software: Evolution and Process, 27(8), 565-572. (Year: 2015).*

International Application No. PCT/US2018/024114, filed Mar. 23, 2018, PCT Search Report and Written Opinion dated Jun. 11, 2018, 9 pages.

* cited by examiner

700

710 Property 1
Name: Treatment ID
Description: A unique id generated for every treatment
Data Type: Text
Validation Rules: Must be present, Begins with "T", Has Length of "8"
Access Rules: Visible to Patient, Clinician 720 Property 2
Name: Serial Number
Description: the serial number of the device to allow to associate the treatment to a patient
Data Type: Text
Validation Rules: Must be present, Begins with "330"
Access Rules: Visible to Patient, Clinician 730 Property 3
Name: Treatment Start Date
Description: The data and time the treatment started
Data Type: DateTime
Validation Rules: Must be present
Access Rules: Visible to Patient, Clinician 740 Property 4
Name: Treatment End Date
Description: The data and time the treatment ended
Data Type: DateTime
Validation Rules: Must be present
Access Rules: Visible to Patient, Clinician 750 Property 5
Name: Air Flow Rate
Description: The average rate of the airflow
Data Type: Number
Validation Rules: Must be present
Access Rules: Visible to Clinician 760 Property 6
Name: Air Pressure
Description: The average air pressure being applied
Data Type: Number
Validation Rules: Must be present
Access Rules: Visible to Clinician 770 Property 7
Name: System Quality of Sleep
Description: The Quality of Sleep metric generated by the system
Data Type: Number
Validation Rules: Must be present
Access Rules: Visible to Patient, Clinician 780 Property 8
Name: Patient Quality of Sleep
Description: The Quality of Sleep metric provided by the patient
Data Type: Enumeration (Bad, Ok, Great)
Validation Rules: None
Access Rules: Visible to Patient, Clinician

Figure 2B

SYSTEMS AND METHODS TO AUTOMATE TRANSFER, STORAGE, AND ANALYSIS OF MEDICAL DEVICE DATA

BACKGROUND OF THE INVENTION

The present disclosure relates to systems and methods for providing automated generation of software for transfer of data from medical devices, storage of the transferred data, and for access to stored medical device data.

In one aspect, the disclosure involves systems and methods for automated generation of medical device communication software and user interface software for accessing medical device data that meets one or more medical device standards set by government or industry regulatory bodies. In one aspect, systems and methods of cloud-based storage of medical device data meeting governmental and/or industry regulatory standards for medical devices are provided.

Various embodiments of the present disclosure include software generation modules for automated generation of one or more of standards-compliant communication software, data storage software, and user access software, as well as methods for automatically generating such standards-compliant software.

Medical devices having electrical elements to obtain, process or store data to diagnose, monitor, or treat a wide range of medical conditions have become critical elements in providing proper medical care to patients. As used herein, the term "electrical medical device" (EMD) refers to a device having one or more electrical components and which is used in the diagnosis, monitoring, or treatment of a medical condition or disease. Such devices may include one or more sensing elements to obtain patient body data or may alternatively receive body data from another medical device for processing, storage, or communication to healthcare providers, patients, and monitoring stations. To perform these activities, many EMDs include processors or other circuitry to receive, analyze, transmit and store information, and may include software in a variety of programming languages.

The increasing complexity of EMDs has led government regulatory authorities such as the US Food and Drug Administration (FDA) and similar bodies in other countries or regions to promulgate standards and regulations to ensure their safety and effectiveness. Such standards and regulations are intended to ensure safety, efficacy, and reliability of numerous aspects of the life cycle of EMDs, including without limitation their design, testing, manufacture, distribution, marketing, and post-market assessment. Compliance with the extensive regulatory requirements for EMDs adds significant cost and time to the overall development process.

One aspect of the foregoing regulations involves standards for medical device communications and storage. Many EMDs include software or hardware interfaces enabling the device to wirelessly exchange data with other computing devices, such as a handheld patient or healthcare provider device (e.g., a patient monitoring device or a physician programmer for the EMD), a cellular network, or a cloud-based server. Because EMD standards and regulations are intended to ensure a high degree of reliability and security, complying with the standards may cost thousands or millions of dollars and result in months or even years of delay to the overall development process. These communications interfaces are developed as a custom program or a series of software modules from scratch by software engineers or developers in particular programming languages for each particular device. Compliance with applicable standards and regulations are essentially built in to the software throughout the development, testing, verification and validation processes—but at relatively high cost and lengthy timeframes.

To permit wireless data exchange between the EMD and other devices or storage, the EMD software developers must develop one or more communications interface to comply with the communication protocols and standards followed by each external device or service to which the EMD connects.

For example, for an EMD to wirelessly connect to a cloud-based server, the EMD software developers must manually write a piece of adapter software for the medical device that adapts the internal data structure of the EMD application software (e.g., embedded software in a body-worn or implantable EMD) to the software interface standards and protocols required for data exchange with the cloud-based servers. Such a task requires programming expertise and can be time consuming, specifically when one must consider management of a variety of network conditions such as network not available, service not available, service not reliable, etc. On top of these challenges, which are applicable to cloud-based communication with any electronic device, the EMD must also comply with applicable medical device regulatory (e.g., FDA, Health Canada, European MDD) and industry (e.g., ISO 13485, IEC 82304, ISO 14971) standards.

Currently, many EMDs communicate data to other electronic devices, such as patient or physician handheld devices. Such communications, which may occur using, e.g., Bluetooth® (Bluetooth SIG, Inc., Kirkland, Wash.) communication protocols, are vulnerable to unauthorized access, commonly referred to as "hacking." In many such EMDs currently on the market, communication with local (non-cloud) devices such as a patient handheld device or physician programmer is facilitated by custom software interface(s) that enable the operating software of the EMD to communicate and exchange data with each type of external device (e.g., patient or physician handheld devices). Thus, to allow the EMD to communicate with a patient handheld, a physician programmer, and a central database, three separate custom interfaces must be developed, each compliant with applicable regulatory communications standards.

Each of these custom interfaces must specify the extent of data exchange with the particular external device. For example, the EMD's patient interface software must include rules governing which data may be accessed by the patient, which may differ from the data that may be accessed by the physician. There is a need for systems that can reduce the cost and time required to develop standards-compliant communications interface software for EMDs. There is also a need for systems that provide a more secure data path, both for storage of data from the EMD as well as for access to such data by external devices, than is presently available. There is a need for systems that can develop robust and secure interfaces for a variety of EMD user devices in a simpler and faster process than provided by the current state of the art.

With an increasing number of EMDs capable of wireless data exchange, security concerns over the potential for unauthorized access ("hacking") into the device have arisen. These include identify theft and heath data privacy when unauthorized data is obtained, as well as the more serious health and safety risks if the performance of the EMD is altered or interrupted. For many EMDs such as pacemakers, defibrillators, and insulin pumps, tampering with the function of the device could lead to serious adverse health consequences or even death. Moreover, each additional external device to which the EMD is capable of communicating adds another potential site of entry for hackers.

One aspect of the foregoing security concerns involves where and how the EMD's data is stored or maintained. To reduce size and weight, data storage for many EMDs (e.g., body-worn or implanted EMDs) is limited and security features are often poor. Currently, many EMDs retain vulnerable data logs in memory within the EMD until the data is manually downloaded, e.g., to a handheld device during an office visit to the treating physician. This creates a relatively long period in which EMD data is exposed to hacking. Accordingly, there is a need for EMD data exchange systems with improved security features and improved storage systems to control data access.

In another aspect, government and industry regulations involve standards for the design and testing of software that analyzes EMD data to provide useful medical information to a user, which may be a patient, a healthcare provider, or a device manufacturer monitoring the function and reliability of its devices. Analysis of data received from an EMD may involve, for example, sensing, buffering, processing, storing, analyzing, and transmission of patient body data or device operational data, and performing various computations to determine medical information regarding the patient's condition, reliability of the EMD, etc. Such data analysis software, like the communication interfaces, are typically developed as custom software modules by software developers at high cost and with lengthy development timeframes driven by the rigorous design and testing standards applicable for many EMDs.

Although systems of the present invention may be described for particular EMDs and EMD systems, persons of skill in the art having the benefit of the present disclosure will appreciate that these systems may be used in connection with other EMDs not specifically noted herein. Accordingly, the particular embodiments disclosed above are illustrative only, as the invention may be modified and practiced in different but equivalent manners apparent to those skilled in the art having the benefit of the teachings herein. Examples, where provided, are all intended to be non-limiting. Furthermore, exemplary details of construction or design herein shown are not intended to limit or preclude other designs achieving the same function. It is therefore evident that the particular embodiments disclosed above may be altered or modified and all such variations are considered within the scope and spirit of the invention, which are limited only by the scope of the claims.

SUMMARY

In one aspect the present invention comprises a system for automated generation of interface software for data transfer between an electrical medical device (EMD) (20) and a data storage medium (DSM) (44), comprising: a medical device modeler (50) for receiving an input defining one or more EMD properties, the medical device modeler (50) comprising a property validator module (220) to test each EMD property with at least one validation test and produce an EMD data model (60) comprising a set of validated EMD properties (232, 234); and an EMD interface generator module (70) for automatically generating, based on the EMD data model (60): an EMD application communication interface (80) comprising software in a first desired computer language to allow an EMD (20) to transmit data to a DSM (44) and receive data transmitted from the DSM (44); and a central communication interface (85) comprising software to allow the DSM (44) to transmit data to the EMD (20) and receive data transmitted from the EMD (20).

In one aspect, the present invention comprises a system for automated generation of interface software for transfer of data between a user device (32, 34, 36) for an electrical medical device (EMD) (20) and a data storage medium (DSM) (44) in communication with the EMD, comprising: a medical device modeler (50) for receiving an input defining one or more EMD properties, the medical device modeler (50) comprising a property validator module (220) to validate each EMD property and providing an EMD data model (60) comprising a set of validated EMD properties (232, 234); and a user device interface generator module (30) for automatically generating, based on the EMD data model (60), a user device interface (31, 33, 35) comprising software to allow a user device (32, 34, 36) to receive EMD data transmitted from a DSM (44) and transmit data to the DSM (44) for transmission to the EMD (20).

In one aspect, the present invention relates to a system for automated generation of interface software for an electrical medical device (EMD) and a storage medium, comprising: a medical device modeler for receiving an input defining one or more EMD properties, the medical device modeler comprising a property validator module to validate each medical device property and providing an EMD data model comprising a set of validated medical device properties and property rules; an EMD interface generator module for automatically generating, based on the EMD data model, an EMD communication interface to allow an EMD to transmit data to the system, and a system interface to receive data transmitted from the EMD; and a storage medium for storing data received by the system interface.

In one aspect, the present invention relates to a system for automated generation of interface software for a user device for obtaining electrical medical device (EMD) data from a storage medium, comprising: a medical device modeler for receiving an input defining one or more EMD properties, the medical device modeler comprising a property validator module to validate each medical device property and providing an EMD data model comprising a set of validated medical device properties and property rules; and a user device interface generator module for automatically generating, based on the EMD data model, at least one user device interface to allow a user device to access EMD data from a storage medium.

In one aspect, the present invention relates to a system for automated generation of software for analyzing electrical medical device (EMD) data, comprising: a storage medium having stored data obtained from an EMD; and a machine learning algorithm module for automatically analyzing stored data from an EMD using machine learning and for generating machine learning algorithm reports, wherein the machine learning algorithm module automatically performs at least one task using the stored data obtained from an EMD, the at least one task selected from identifying trends in the data, generating alerts that may be forwarded to a user, classifying disease states, identifying patient status, generating decision trees, and wherein the machine learning algorithm automatically stores the machine learning algorithm reports in the storage medium.

In one aspect, the present invention relates to a system for automated generation of software by a software designer/system user for analyzing (EMD) data, comprising: a storage medium having stored data obtained from an EMD; an algorithm editor for receiving an input defining an algorithm; and an algorithm execution module for executing the algorithm using the stored data obtained from an EMD, wherein the algorithm execution module automatically generates user reports and stores the user reports in the storage medium.

In one aspect, the present invention comprises a method for automated generation of interface software for data transfer between an electrical medical device (EMD) (20) and a data storage medium (DSM) (44), comprising: receiving an input defining one or more EMD properties; testing each EMD property with at least one validation test; producing an EMD data model (60) comprising a set of validated EMD properties (232, 234) based on said testing; and automatically generating, based on the EMD data model (60): an EMD application communication interface (80) comprising software in a first desired computer language, wherein said software is capable of allowing an EMD (20) to transmit data to a DSM (44) and receive data transmitted from the DSM (44); and a central communication interface (85) comprising software capable of allowing the DSM (44) to transmit data to the EMD (20) and receive data transmitted from the EMD (20).

In one aspect, the present invention comprises a method for automated generation of interface software for transfer of data between a user device (32, 34, 36) for an electrical medical device (EMD) (20) and a data storage medium (DSM) (44) in communication with the EMD (20), comprising: receiving an input defining one or more EMD properties; testing each EMD property with at least one validation test; producing an EMD data model (60) comprising a set of validated EMD properties (232, 234) based on the testing; and automatically generating, based on the EMD data model (60), a user device interface (31, 33, 35) comprising software to allow a user device (32, 34, 36) to receive EMD data transmitted from a DSM (44) and transmit data to the DSM (44) for transmission to the EMD (20).

BRIEF DESCRIPTION OF THE DRAWINGS

FIG. 2B is a diagram of a group of EMD property blocks entered by a user into a Device Modeler for an electronic medical device.

DESCRIPTION

Figure 1A:
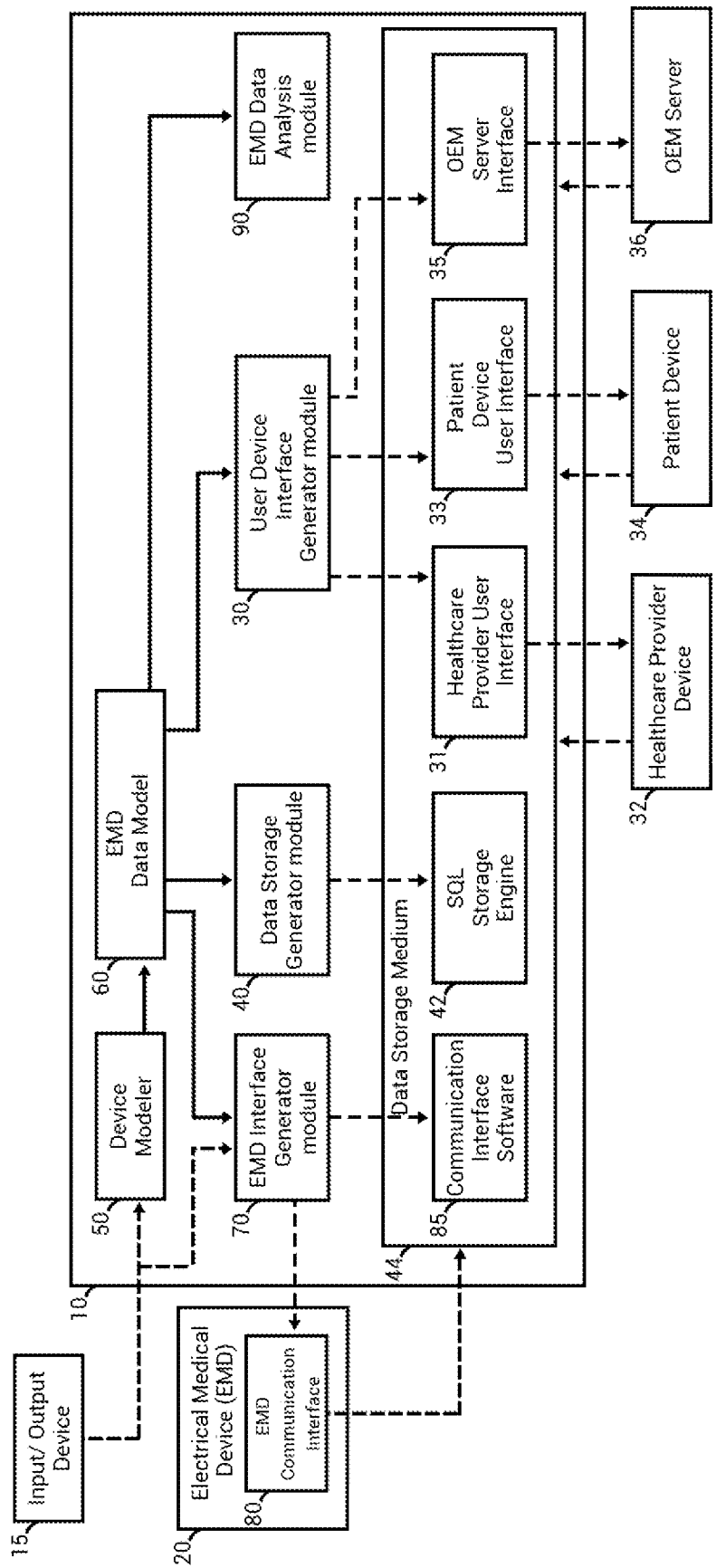
FIG. 1A is a diagram of an embodiment of a system for automated generation of medical device software.

Exemplary embodiments are illustrated in referenced Figures of the drawings. The embodiments disclosed herein are considered illustrative rather than restrictive. No limitation on the scope of the technology and on the claims that follow is to be imputed to the examples shown in the drawings and discussed here.

Embodiments of the present disclosure include systems and methods for automatically generating of one or more of communications interface software, data storage software, and data analysis software for electrical medical devices (EMDs). In one aspect, the disclosure involves a software development system for automatically generating communication software for standards-compliant data exchange between an EMD and an EMD data storage system, based on a developer-defined model of the EMD. In one embodiment, the disclosure provides systems and methods for automatically generating a communications interface for the transmission and storage of data from an EMD to an EMD data storage unit.

In another aspect, the disclosure involves a software development system for automatically generating communication software for standards-compliant data exchange between an EMD user device (e.g., a patient or physician/healthcare provider handheld, or an EMD manufacturer database) and an EMD data storage system, based on a model of the EMD defined by a system user. In one embodiment, the invention provides systems and methods for automatically generating a communications interface for allowing an EMD user device to access stored EMD data from an EMD data storage unit.

In a further aspect, the invention involves a software development system for cloud-based, standards-compliant storage of EMD data in an EMD data storage unit. In one embodiment, the invention provides a software development system having centralized data storage for EMD data. In one embodiment, the centralized storage is scalable to handle an increasing number of devices and increasing data volumes.

In another aspect, the present disclosure provides a software development system for the automated analysis of data received from an EMD. In one embodiment, the invention provides systems and methods for automatically generating software to analyze EMD data according to an analysis model of the EMD defined by a system user.

In a still further aspect, the present disclosure provides a software development system for automatically generating communication software for standards-compliant data exchange between an EMD and an EMD user device. In different embodiments, the invention provides a first software interface for operation in the EMD and a second software interface for operation in the EMD user device, which may comprise one or more of a patient device used by the patient to exchange data with the EMD, a healthcare provider device used by a healthcare provider (e.g., a physician) to program and/or retrieve data from the EMD, and an original equipment manufacturer (OEM) server such as a database maintained by the EMD manufacturer for retrieving data from the EMD and/or transmitting software updates to the EMD.

FIG. 1 illustrates one embodiment of a system 10 for automated generation of software for data exchange with an electronic medical device (EMD) 20. As used herein, software refers to computer code in a programming language independent of the computing system in which it operates, and includes firmware operating within a processor in an EMD. In various embodiments, the data exchange may involve one or more of sending data to the EMD 20, receiving data from the EMD, storing data received from the EMD, and storing data to be transferred to the EMD. In a further embodiment, the system may involve automated generation of software for analysis of patient or EMD status data. The system 10 may automatically generate one or more of 1) communication software (e.g., interfaces 80, 85) for data exchange between an EMD 20 and a data storage medium 44; 2) data storage software 42 for secure storage of EMD data in a data storage medium 44; 3) communication software (e.g., interfaces 31, 33, 35) for one or more EMD user devices (e.g., healthcare provider device 32, patient device 34, and OEM server 36) to exchange data with the EMD via data storage medium 44; and 4) data analysis software (e.g., data analysis module 90) for analysis of EMD 20 data to provide useful medical information for an EMD user (e.g., a physician or patient).

Healthcare provider device 32 may be any of a variety of computing devices (e.g., a cellphone, a tablet computer, a laptop computer, etc.) used by a healthcare provided such as a physician to exchange data with an EMD 20 coupled to a patient's body. The healthcare provider device 32 may be used, without limitation, to program the EMD 20 or to retrieve EMD data. EMD data may include data relating to the health status of the patient (e.g., one or more patient body parameters measured or calculated by the EMD such as inspiration or expiration, respiratory rate, heart beats, heart rate, blood glucose levels, blood pressure, temperature, patient activity levels as measured by an accelerometer, etc.) as well as data relating to the operating status or error status of the EMD (e.g., power or battery level or status, error logs, error count or rate, etc.). Patient device 34 may be any of a variety of computing devices to enable a patient to exchange data with the EMD 20. Patient device 34 may be used, without limitation, to perform some or all of the functions allowed by the healthcare provider device 32. In some embodiments, the patient device 34 may permit a more limited data exchange with the EMD 20 compared to the healthcare provider device 32. OEM server 32 may be any of a variety of computing devices, but in one embodiment is a data server for data exchange with a plurality of medical devices 20 manufactured by an original equipment manufacturer ("OEM") of the EMD.

In the embodiment illustrated in FIG. 1, EMD user devices 32, 34, 36 are designed for indirect communication with medical device 20 via a data storage medium 44. In many current devices, EMD user devices such as these communicate directly with the EMD 20. While such direct communication has certain advantages, it generally requires that a custom interface be developed by each individual type of device that must communicate with the EMD, which may time consuming and costly. The system of FIG. 1 overcomes these disadvantages by providing an automatically generated interface that is simplified to communicate not with the EMD 20, which may vary significantly in construction and architecture from once type of EMD to another (e.g., a heart monitor vs. a continuous positive airway pressure (CPAP) machine), but with a data storage medium 44 that may be the same regardless of the type of EMD 20 for which data exchange is needed. Such a system facilitates a wider variety of users to access the EMD data because the data is securely maintained in a central repository. It also facilitates improved data analysis of multiple patients and patient groups because all of the data is available for analysis at a single location in a standardized and secure format. Similarly, identification and resolution of design or operational issues with the EMD 20 may be facilitated because diagnostic and operational data from the EMD is likewise maintained in a central, secure storage medium. Thus, diagnosis of potential failures for individual EMDs as well as all EMDs of a particular type or class is made easier.

While not shown in FIG. 1, in alternative embodiments, interfaces may be automatically generated that permit EMD user devices (e.g., 32, 34, 36) to communicate directly with an EMD 20.

In one embodiment, the system 10 includes a Device Modeler 50 that allows a software developer to create an EMD Data Model 60 of the EMD 20 using simple configurable data property input blocks. The EMD Data Model 60 is a collection of data property features and property rules that describe the data being transmitted from an EMD 10 to the system 10. The EMD Data Model 60 can be readily modified by a software developer/system user during an EMD 20 development project as the data to be generated by or exchanged with the EMD 20 changes over time (e.g., as the design of the EMD 20 is modified or changed during the development process). The EMD Data Model 60 is used by one or more additional software generator modules (e.g., 30, 40, 70, 90) to provide automated generation of software interfaces for communications or data analysis.

In one embodiment, the Device Modeler 50 is a software program accessible via an input/output device 15 (e.g., a computer keyboard or terminal) that allows a software developer to configure the EMD Data Model 60 by specifying the property features such as the type of data (e.g., number data, text data, image data) to be exchanged between the EMD 20 and storage medium 44, or between the EMD and other devices (e.g., healthcare provider device 32, patient device 34, OEM server 36) via storage medium 44, and the property rules applied to that data (e.g., the data must be present, must be within a specified range, etc.).

Once the EMD Data Model 60 is specified by the software developer using the Device Modeler 50, the EMD Data Model 60 may be used by a plurality of modules to generate various software interfaces. In one embodiment, an EMD Interface Generator (EMDIG) module 70 automatically generates the computer code for the EMD application communication interface 80 to allow exchange of data between EMD 20 and data storage medium 44. The EMD application communication interface 80 comprises software or firmware that is configured to be loaded into and operate within the EMD 20 (e.g., as embedded software) to facilitate communication between the EMD 20 and data storage medium 44.

The EMDIG module 70 automatically generates the EMD application communication interface software 80 in a desired programming language (e.g., C, C+, C++, C#, Java, etc.) and operating system platform (e.g., Windows, Linux, Microcontrollers, etc.). The EMD application communication interface software 80 includes mitigations for common communication issues such as no network available, no service available, etc., and is compliant with important regulatory and industry standards specific for the EMD 20. In one embodiment, once it is generated by EMDIG module 70, the EMD application communication interface software 80 may be stored for later uploading/embedding in, e.g., a processor in the EMD 20.

The EMDIG module 70 also generates a complimentary central communication interface software 85 for a data storage medium 44. The central communication interface software 85 comprises software or firmware configured to be located and operate within the data storage medium (e.g., as embedded software) to facilitate communication between the EMD 20 and the data storage medium 44. In one embodiment, the central communication interface software 85 receives data sent by the EMD 20 via the EMD application communication interface software 80 and stores the data in the data storage medium 44. In one embodiment, the data may be stored in data storage medium 44 using a storage engine 42 also developed based on the EMD Data Model 60. In one embodiment, central communication interface software 85 allows the transmission of data (e.g., commands, software updates, etc.) from the data storage medium 44 to the EMD 20. Data transmitted to the EMD 20 from the data storage medium 44 using the central communication interface software 85 may include data received from another device (e.g., healthcare provider device 32, patient device 34, or OEM server 36).

In one embodiment, the EMD application communication interface software 80 and the central communication interface software 85 are compliant with class III medical device standards and regulations, which govern implantable medical devices (e.g., implantable pacemakers and defibrillators) and provide the most stringent standards. In an alternative embodiment, the EMD application communication interface software 80 and the central communication interface software 85 generated by the EMDIG module 70 comply with the standards of a selected regulatory class (e.g., class I, II or III standards) for medical devices. In one embodiment, the EMD application communication interface software 80 generated by the EMDIG module 70 also includes code to allow for batch data exchange, which allows data transfer between the EMD application communication interface software 80 and the central communication interface software 85 based on, e.g., a predetermined time or time period since a prior exchange, or when a certain amount of data is available for exchange (e.g., 100 records, 100 MB of data, etc.). In another embodiment, the EMD application communication interface software 80 facilitates individual data set exchange, allowing the EMD 20 to exchange data between the EMD application communication interface software 80 and the central communication interface software 85 of the data storage medium 44 whenever it is available.

In one embodiment, the EMD Data Model 60 is used by an EMD User Device Interface Generator (UDIG) module 30 to automatically generate software for one or more EMD User Device Interfaces 31, 33, 35. Each EMD User Device Interface (UDI) provides software enabling a particular class of EMD user devices (e.g., healthcare provider device 32) to access EMD data appropriate for that class of devices from a storage medium 44. In one embodiment, each UDI 31, 33, 35 is a simplified interface that displays an interactive webpage in the corresponding EMD user device. The interactive webpage interface allows the EMD user to exchange data with the EMD 20 via a data storage medium 44 acting as an intermediary between the EMD user device 32, 34, 36 and the EMD. The EMD user may, for example, send commands or programming to the EMD 20, receive patient data from the EMD, or receive EMD diagnostic data indicating the operational status of the EMD.

In one embodiment, each UDI 31, 33, 35 comprises automatically generated computer software in an interface language (e.g., Hyper Text Markup Language (HTML), Cascading Style Sheet (CSS), or JavaScript (JS)), and is tailored so that the corresponding EMD user device 32, 34, 36 accessing data using the interface sends or receives from the storage medium 44 only a particular set of information (e.g., text, graphs, commands, data requests, etc.) appropriate for that EMD user device. In one embodiment, the UDIs 31, 33, 35 created by the UDIG module 30 are compliant with class III medical device standards and regulations, while in alternative embodiments, they are compliant with the standards of a selected class (e.g., class I, II, or III).

As a non-limiting example, based on the EMD Data Model 60, the UDIG module 30 may create software defining UDI 31 to allow a healthcare provider device 32 to request specific types and volumes of data from the storage medium 44 to diagnose, monitor, or treat the patient's medical condition, and in addition send commands, programming parameter changes, or software updates to the EMD 20 through the UDI 31 to the storage medium 44, which may store the commands or route them directly to the EMD 20 through the central communication interface software 85 and the EMD application communication interface software 80. A similar but different UDI 33 may comprise software allowing a patient access to a more limited amount of information and/or EMD 20 operating parameter settings through a patient device 34. For example, the UDI 33 may preclude the patient from changing the operating parameters of the EMD 20 or may limit the patient's control over operating parameters to a predetermined range, compared to a much larger range of operational settings available to a healthcare provider via the UDI 31 and healthcare provider device 32.

It will be understood that storage in a plurality of different storage media 44 locations may be specified, even though for simplicity only a single data storage medium 44 is illustrated in FIG. 1. Likewise, separate data storage media 44 may be provided for storage of all UDIs of a particularly type of EMD user device (e.g., healthcare provided devices 32). In other embodiments, separate data storage media 44 may be provided for a plurality of user devices based on other parameters (e.g., geographical location of the user devices) in addition to or instead of the type of EMD user device. As a non-limiting example, the UDIs for all EMD user devices located in a particular city, state, multistate region, or country may be stored in a single central storage medium 44.

Referring again to FIG. 1, in one embodiment, a Data Storage Generator (DSG) module 40 uses the EMD Data Model 60 to automatically generate a data storage schema for use in storing EMD data in the data storage medium 44 as a database. In one embodiment, DSG module 40 using a SQL (Structured Query Language) engine 42 to generate a SQL storage schema. The EMD 20 data is stored and maintained in the database in compliance with existing FDA and privacy regulations and statutes. The DSG module 40 automatically provides a SQL data schema appropriate for rapid search and retrieval of data. The SQL data schema can be applied to a standard SQL database engine (or similar database engines) to create a structured storage database for the data transmitted by the EMD 20 to the data storage medium 44. In one embodiment, the generated SQL data storage schema has constraints and relationships defined to protect data integrity and record data changes to create an audit trail compliant with a requirement of many privacy regulation and statutes (e.g. HIPAA). In one embodiment, the SQL data schema automatically generated by DSG module 40 is compliant with class III medical device standards and regulations, while in alternative embodiments, it is compliant with the standards of a selected class (I, II, or III).

In alternative embodiments (not shown) DSG module 40 may generate data storage schemas according to different storage architectures instead of SQL. These storage architectures may include, without limitation, NoSQL, NewSQL, or other hybrid systems incorporating features of both SQL and NoSQL. Additional details on the generation of a SQL (or NoSQL, etc.) storage engine 42 are provided in the discussion of FIG. 4.

Contrary to conventional systems that permit relatively unsecure data retrieval by EMD user devices 32, 34, 36 directly from an EMD 20, some embodiments of the prevent disclosure provide a two-step data storage and retrieval process. First, data from the EMD 20 is securely transferred, via the EMD application communication interface software 80 and the corresponding central communication interface software 85, to a data storage medium 44. In some embodiments, additional data analysis may be performed by Data Analysis software 95 and stored in a data storage medium 44. Second, the data is securely retrieved from the data storage medium 44 by EMD user devices 32, 34, 36 via the UDIs 31, 33, 35. By separating the steps of data storage from the EMD 20 and retrieval of stored data by EMD user devices 32, 34, 36, improved security and reliability may be obtained because all of the data is securely maintained in a centralized medium in a standardized format. In addition, by allowing an automated EMD User Device Interface Generator (UDIG) module 30 to automatically generate the UDI software 31, 33, 34 based on the EMD Data Model 60, the improved security of standardized interfaces may be obtained in a simplified manner. In one embodiment, each interface comprises a web-based interface using standards such as HTML, CSS, and JavaScript that work across a variety of browsers, device types, and operating systems. In addition, standardization is made easier because all of the interfaces communicate with a central storage medium having a single programming and data storage format.

Figure 1B:
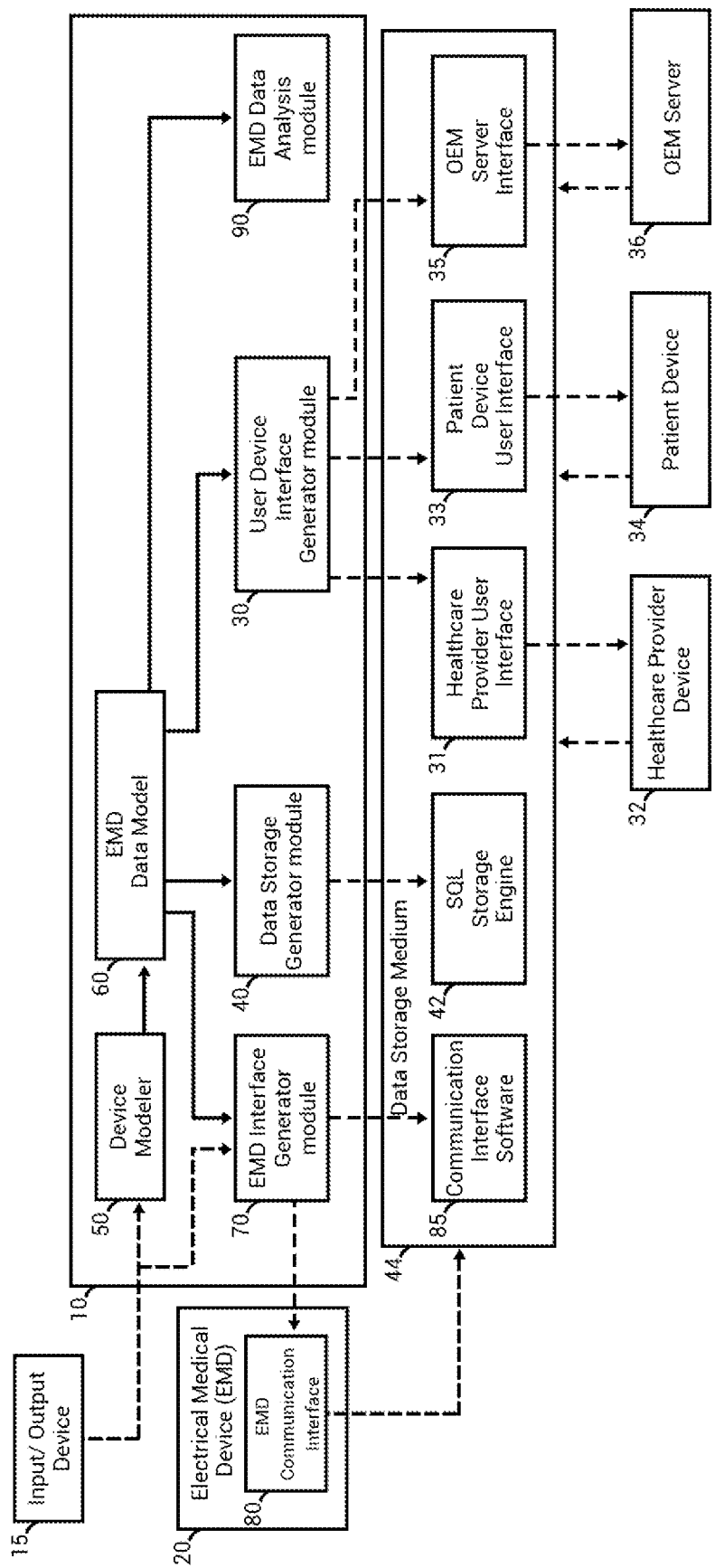
FIG. 1B is a diagram of another embodiment of a system for automated generation of medical device software.

FIG. 1B provides an alternative embodiment of a system for automated generation of medical device software. The modules and functions of FIG. 1B are similar to those of FIG. 1A. However, the system of FIG. 1B includes a software development system 10 for automated generation of medical device software, as well as an EMD communication system using the automatically generated medical device software produced by the system 10. In particular, the software interfaces (80, 85, 31, 33, 35) and storage engines (42) produced by the system 10 are used in an EMD 20, data storage medium 44, and user devices 32, 34, 36 that are separate from the software development system 10. Accordingly, FIG. 1B illustrates an EMD communication system in which the data storage medium 44, which operates as an intermediary between EMDs 20 and user devices 32, 34, and 36, may be at a different location than the automated software development system 10, and may operate independently of the automated software development system 10.

Figure 2A:
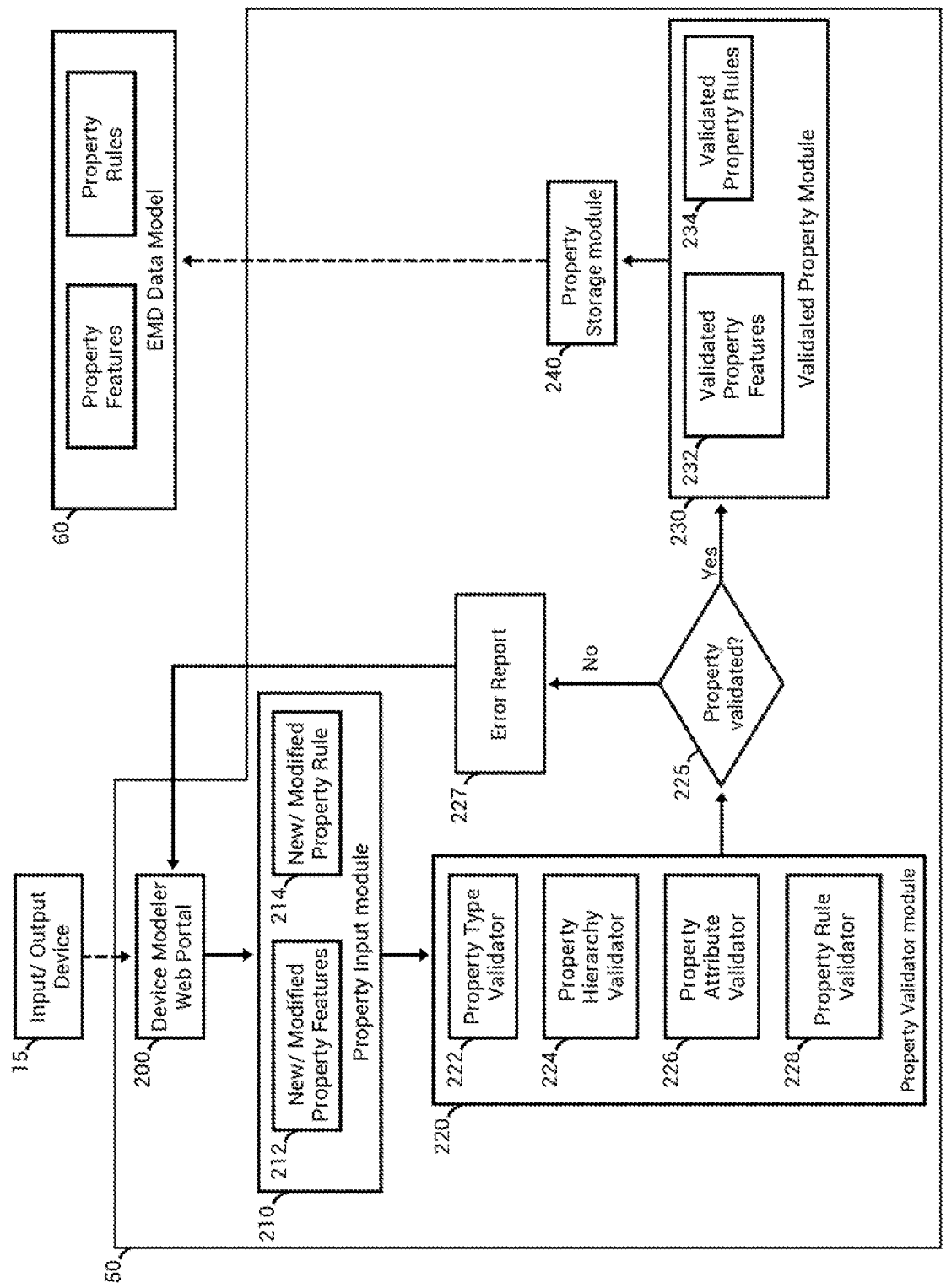
FIG. 2A is a diagram of an embodiment of a Device Modeler for an electronic medical device for use in automated generation of medical device software.

FIG. 2A illustrates one embodiment of a Device Modeler 50 (FIGS. 1A, 1B) for use by a software developer to create an EMD Data Model 60 of data to be stored, communicated, or calculated by one or more of the EMD 20, a data storage medium 44 in communication with the EMD, and a user device (e.g., 32, 34, 36) intended for interaction with the EMD 20. Systems of the present invention allow a system user/software developer to create a high-level model of various data to be exchanged, processed (e.g., calculations performed), or stored in one or more of the EMD 20, a user device (e.g., 32, 34, 36), and a data storage medium 44 acting as an intermediary between the EMD 20 and the user device(s).

The EMD Data Model 60 is based upon defined EMD properties that describe the data to be transferred or determined (property features) and the conditions of transfer (property rules). A software developer, alternatively referred to as a system user for simplicity, may access the Device Modeler 50 via a device modeler web portal 200 using an input/output device 15. A property input module 210 receives system user inputs to specify the EMD properties. Each EMD property that is specified includes property features and property rules.

The property features may include information such as the property data type (e.g., numbers, date, time, text, images, videos, etc.), property parameters or attributes (e.g., property name, size, frequency of upload, etc.) for the selected property type, as well as a property hierarchy which may involve, e.g., defining a property as a parent property or a child property. Exemplary property rules may include validation rules (e.g., values must be within a defined range), access rules (e.g., only a physician or device manufacturer may access that property), and calculation rules (e.g., a formula for calculation of respiration rate from one or more pressure sensors, or calculation of heart rate or heart rate variability from a sequence of R-R intervals).

In one embodiment, a system user specifies each EMD property as a single EMD property block comprising both property features and property rules. In alternative embodiments, the system user/developer specifies the property features and property rules as separate entries. In one embodiment, the system user may use the Device Modeler 50 to create EMD property blocks that are unique to the system user's EMD. In one embodiment, Device Modeler 50 may include predefined property blocks that may be selected by the user, avoiding the need to create a new property block. Predefined blocks may be provided for common EMD properties such as EMD serial number, EMD patient ID number, heart rate, etc. In some embodiments, both predefined EMD property blocks and user-created EMD property blocks may be selected or created by the developer/system user.

Referring again to FIG. 2A, in one embodiment the property input module 210 separates each EMD property block into property features and property rules. The EMD property features are processed by a property feature module 212. The property input module 210 further includes a property rule module 214, which stores the rule portion of each EMD property.

When the system user/software developer has specified the EMD properties and their respective features and rules in the property input module 210, a property validator module 220 is used to validate each EMD property and their corresponding rules. The property validator module 220 may include one or more modules to validate one or more aspects of the property features (e.g., property types, property parameters, property attributes) and property rules configured in the property input module 210.

In one embodiment, the property validator module 220 includes a property type validator module 222, which validates the property types (one aspect of a property's features) for each configured property. As non-limiting examples, property type may include number, text, image, videos, etc. In one embodiment, the property type validator module 222 operates to ensure that the property type is a known type of property. In one embodiment, the property type validator module 222 ensures that other information for the EMD property is compatible with the property type. As a non-limiting example, if the EMD property type is an image, but the EMD property includes a rule appropriate only for an EMD having a "number" property type (e.g., the EMD property includes a rule stating that the value must be between 10 and 20), the property type validator module 222 flags the rule as incompatible or erroneous in view of the property type.

In one embodiment, the property validator module 220 includes a property hierarchy validator module 224, which validates the hierarchy (another aspect of a property's features) of each configured property to ensure that the child properties (i.e., sub-properties of other defined properties in a hierarchical relationship) do not violate constraint and attributes of the parent property. As a non-limiting example, if a blood pressure property is configured to be a set of two numbers, the hierarchy validator will ensure that its two sub-properties, systolic and diastolic for example, are both likewise configured to be numbers.

In another embodiment, the property validator module 220 includes one or more property attribute validator module 226, which validates that the parameters/attributes of each property feature are consistent with other parameters/attributes or rules of the property feature. As a non-limiting examples, a property of data type "image" should not have a frame rate (applicable only to video data). In addition, the image size cannot not exceed system maximum size limits for images.

In one embodiment, the property validator module 220 includes a property rule validator module 228, which validates the rules specified for each property and/or sub-property. It will be apparent in light of the present disclosure that in some instances different modules within the property validator module 220 may perform similar or duplicate functions. For example, the property type validator module 222 may include some rule-validating functions, and the property rule validator module 228 may ensure that some of the property attributes, hierarchical data elements, and/or property types for a given EMD property are consistent with the rules for that property block. The embodiments depicted in FIG. 2A are not to be construed as limiting, and various architectures for the property validator module 220 are considered to be within the scope of the present disclosure. More generally, property validator module 220 performs tests on the features and rules defining each property block specified by a software developer/system user in the Device Modeler 50.

Each EMD property block is checked (225) to ensure that it has been fully validated by the property validator module 220. For EMD property blocks that cannot be validated, an error report may be generated and displayed (227; e.g., by an error report generator module) to the system user to facilitate the user to correct the error or resolve any issues that preclude validation. The error report content may vary based upon the particular type of validation failure (e.g., property type invalid, property hierarchy invalid, etc.), the type of EMD, etc. In one embodiment, the error report may include messages describing in detail the nature and cause of the validation failure. In some embodiments, the system user may be provided with one or more prompts or suggestions to correct the error and allow the EMD property block to be validated.

Once EMD property blocks have been validated, as indicated by the "yes" output of block 225 in FIG. 2A, the result is a validated property module 230 which includes a set of validated property features 232 and a set of validated property rules 234.

The validated EMD property blocks in the validated property module 230 are passed to a property storage module 240, which stores the validated EMD property blocks to a database. In one embodiment, the property storage module 240 transforms the hierarchical data in a manner that allows a fast retrieval of the property from the database, even properties that are deep within the hierarchy. In one embodiment, data is stored in a graphical data structure that allows faster retrieval of data properties deeper in the hierarchy. In one embodiment, an index is associated with the graphical data structure, allowing for faster searching and retrieval of data regardless of its position in the hierarchy. The completed set of property features and property rules that have been configured, validated and stored collectively defines the EMD Data Model 60. In addition to defining and configuring new properties, the Device Modeler 50 allows a software developer to modify existing properties to alter the device model, e.g., to accommodate design changes during the course of an EMD development project, or for the development of new devices based on prior designs.

FIG. 2B provides a non-limiting example of a number of EMD property blocks defined by a software developer for an electronic medical device (EMD) 20 according to FIG. 1. In the example of FIG. 2A the EMD is a CPAP machine. The group 700 of property blocks includes eight blocks (710-780), each of which describes a different EMD property to be stored, communicated, or calculated by one or more of the EMD 20, a data storage medium 44 in communication with the EMD, and a user device (e.g., 32, 34, 36) intended for interaction with the EMD 20. Each property block 710-780 includes a name, a brief description, a data type, a validation rule, and an access rule.

The property names and descriptions are information that may be validated by the property attribute validator module 226. Each property includes a property data type (e.g., text, number, date/time) that may be validated by the property type validator module 222. The validation rules may indicate, as non-limiting examples, the length of the data to be provided, or initial numbers or letters that must be present for the property to be valid. The access rules indicate the various EMD users to whom the data may be made available, e.g., healthcare provider only, a patient only, both healthcare provider and patient, etc. Both the validation rules and the access rules may be validated by the property rule validator module 228.

Figure 3A:
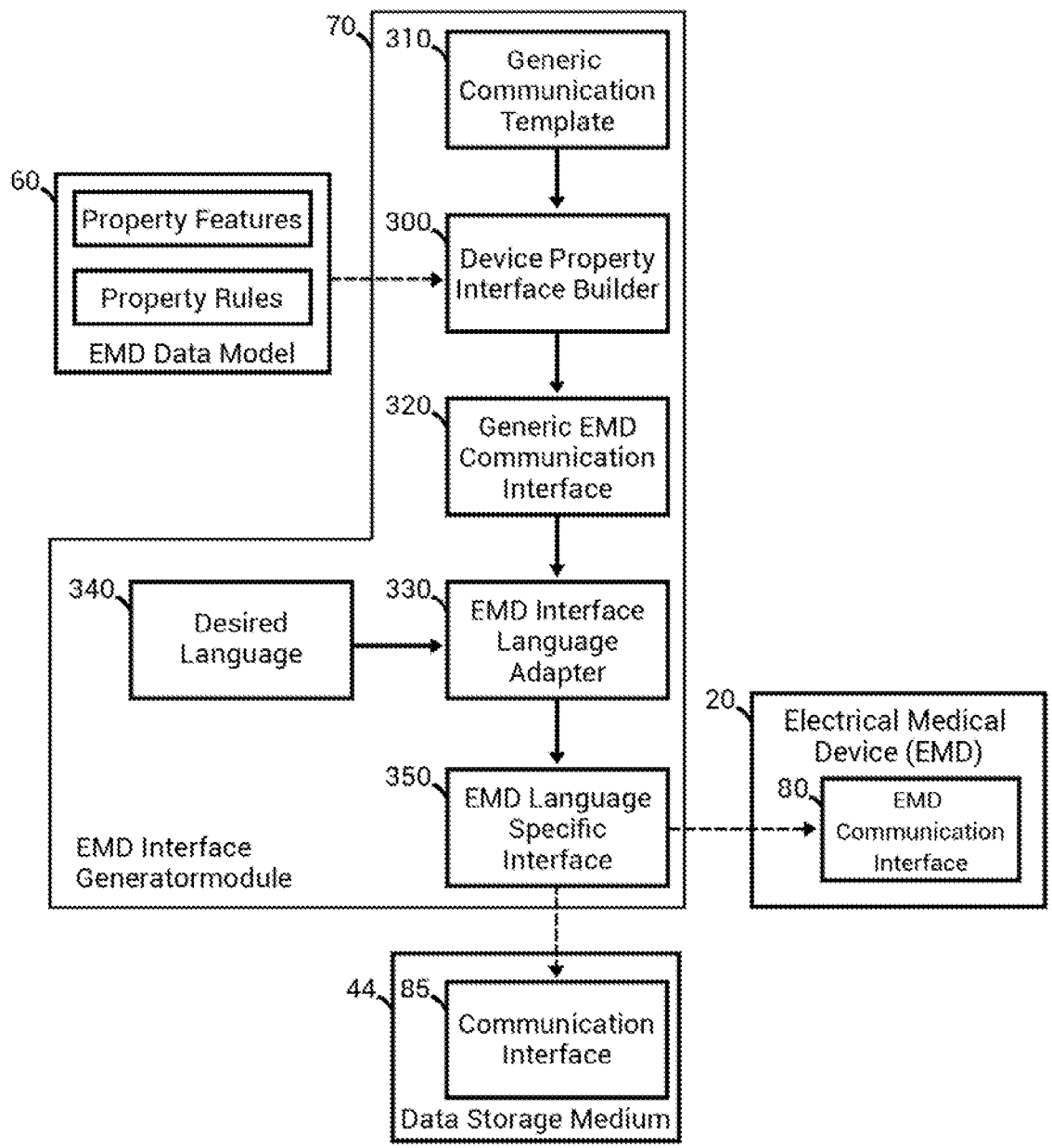
FIG. 3A is a diagram of an EMD Interface Generator module for use in automated generation of medical device interface software.

FIG. 3A illustrates one embodiment of the EMD Interface Generator (EMDIG) module 70 of FIG. 1 for automatic generation of software interfaces for data exchange between an EMD 20 and a data storage medium 44. The property features and property rules from the EMD Data Model 60 are used by the EMDIG module 70 as inputs. The EMDIG module 70 also includes a Generic Communication Template (GCT) 310, which is a file that defines the common data communication rules and methods needed for an EMD interface to allow communication between an EMD 20 and a data storage medium 44, such as connection, transmission, response, error handling, local persistence in the event of no network detection, etc. However, the rules in the GCT 310 are not specific to the EMD 20 data to be transmitted. Because the GCT 310 is independent of the EMD Data model 60 for a particular EMD 20 (e.g., a heart rate monitor, a neurostimulation, or a CPAP machine), the GCT 310 is defined at a high level that is independent of any specific programming language.

A Device Property Interface Builder (DPIB) module 300 is used to automatically adapt the GCT 310 to the validated property features and rules that define the EMD Data Model 60, producing a Generic EMD Communication Interface 320 as an output. The Generic EMD Communication Interface 320 created by the DPIB 300 is a modified version of the GCT 310 that has been adapted to reflect the property features and rules defining the EMD Data Model 60 for a particular EMD 20. These modifications enable the Generic EMD Communication Interface 320 to subsequently be written into a desired programming language by an EMD Interface Language Adapter (EMD ILA) module 330.

A desired programming language 340 is specified by the software developer, and the EMD ILA module 330 adapts the Generic EMD Communication Interface 320 to the desired programming language 340 (e.g., C, C+, C++, C#, Java, etc.) by applying language-specific rules for the programming language specified by the system user/software developer to the Generic EMD Communication Interface 320. For each portion of the Generic EMD Communication Interface 320, the EMD ILA module 330 creates language-specific software to accomplish the associated tasks for that portion of the Generic EMD Communication Interface. For example, a data type of Map is known as HashMap in Java, but Dictionary in C#, and a text element is referred to as String in Java and C# but as char* in C. In addition to mapping the Generic EMD Communication Interface 320 into language-specific software, the EMD ILA module 330 also performs tests on the language-specific software it produces to ensure that the interface will achieve the desired interface functions securely and within design and regulatory constraints specific to the particular EMD design project, as discussed in greater detail in FIG. 3B.

The EMD ILA module 330 generates an EMD Language Specific Interface (LSI) 350 for reliable and secure data exchange between an EMD 20 and a data storage unit 44. In one embodiment, the EMD LSI 350 includes an EMD application communication interface 80 that may be programmed as software or firmware into the EMD 20, and a corresponding central communication interface 85 that may be programmed as software or firmware in the data storage unit 44. The EMD LSI 350 complies with applicable government and industry standards and regulations for electronic medical devices (e.g., class I, II or III medical devices).

Because the EMD LSI 350 created by EMDIG module 70 includes both the EMD application communication interface 80 for use in the EMD 20 and the central communication interface 85 for use in the data storage medium 44, it will be understood that the various modules of EMDIG module 70 may perform similar processes to produce similar but different outputs to obtain both portions of the EMD LSI 350. In addition, it will be understood that, because the computer languages used in the EMD 20 and the data storage medium 44 may be different, the "desired language" 340 may, in some embodiments, include separate languages for the two interface portions (80, 85) of the EMD LSI 350, and that the EMD Interface Language Adapter (ILA) module 330 will perform similar but different processes to produce the two software interfaces for the EMD 20 and the data storage medium 44, respectively.

Figure 3B:
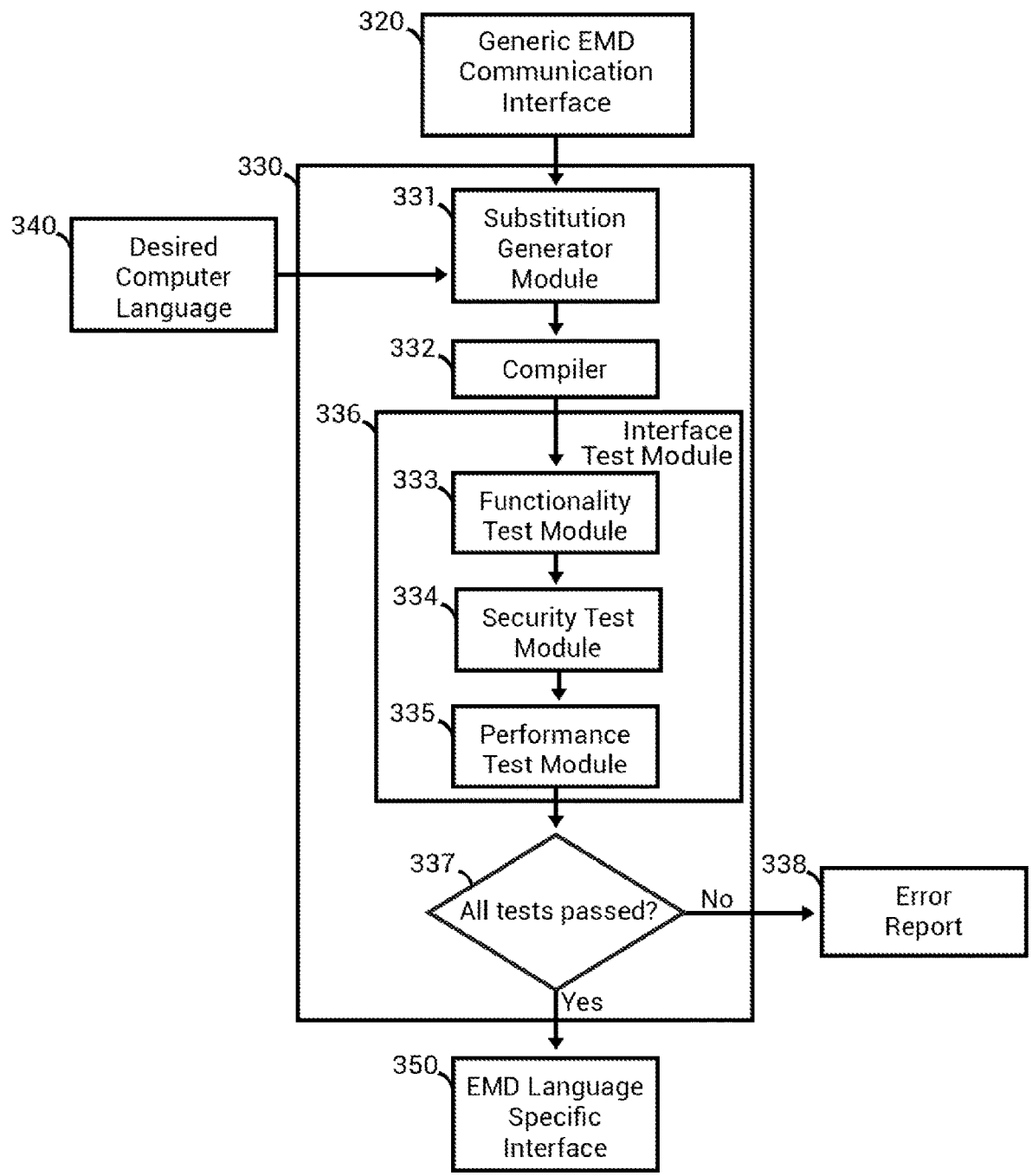
FIG. 3B is a diagram of an EMD Interface Language Adapter module for use in automated generation of medical device interface software.

FIG. 3B illustrates one embodiment of an EMD Interface Language Adapter (EMD ILA) module 330 in the EMDIG module 70 of FIG. 3A. The EMD ILA module 330 includes a Substitution Generator Module 331 to convert each functional portion of the Generic EMD Communication Interface 320 into computer language-specific software (e.g., C, C+, C++, C#, Java, etc.) to implement the functions associated therewith. The desired computer language 340 is specified by the software designer to the EMD ILA module 330 via, e.g., an input/output device 15 (FIGS. 1A, 1B). As previously noted, in some embodiments the software designer may specify different computer languages for the EMD application communication interface 80 and the central communication interface 85. A compiler 332 compiles the computer code for each software portion corresponding to each of the functional portions of the Generic EMD Communication Interface 320 into separate candidate software interface programs for the EMD application communication interface 80 and the central communication interface 85, which together comprise the EMD LSI 350. "Candidate software interface program" refers to a compiled interface program that has not yet been verified to achieve the desired functionality in a secure and reliable manner.

Each candidate software interface program is then subjected to a battery of tests by an Interface Test module (ITM) 336 to verify and/or validate each candidate interface. The ITM 336 includes a Functionality Test module (FTM) 333, a Security Test module (STM) 334, and a Performance Test module (PTM) 335 to test each candidate interface.

The FTM 333 tests the functionality of each candidate interface to ensure that the functional requirements for the data exchanges set forth in the EMD Data Model 60 are achieved by the candidate portions 80, 85 of the EMD LSI 350. These include tests to ensure that the candidate EMD application communication interface 80 for the EMD 20 can successfully transmit data to and receive data from the data storage medium 44 via the central communication interface 85. In one embodiment, the FTM 333 includes tests to ensure that the EMD application communication interface 80 can handle network problems and errors, such as delivery failure, network not available, etc. In one embodiment, the FTM 333 tests the interface in offline mode to ensure that when network problems occur, or if the EMD 20 operating software requests batch operation, the data can be stored locally in the EMD 20 for a configurable time period. In one embodiment, the functionality tests are executed as automated scripts that test each line of the software code of both candidate portions 80, 85 of the EMD LSI 350.

The STM 334 subjects each candidate interface portion 80, 85 to security tests to ensure the security of both the software code and the data to be transmitted. In one embodiment, the STM includes tests to ensure that EMD 20 data cannot be accessed or altered by unauthorized users (e.g., hackers). This includes penetration testing which attempts to inject malicious code and data into the candidate interface portions 80, 85 of the EMD LSI 350 to ensure that the programming flow and functionality are not compromised. In one embodiment, encryption testing is performed to ensure that the data that is stored locally (e.g., while the EMD 20 is in offline mode) is encrypted. In one embodiment, the encryption testing also tests the encryption of data in transit between the EMD 20 and the data storage medium 44. Encryption of data at rest (i.e., in the EMD 20 or storage medium 44) or in transit is required by government regulations such as HIPAA and the EU Data Protection Directive. Accordingly, the testing performed by the STM 334 on the candidate interfaces 80, 85 helps ensure that the interfaces meet important data integrity requirements for medical devices.

The PTM 335 subjects the candidate interface software portions 80, 85 of the EMD LSI 350 to performance tests to ensure that they meet the memory, CPU, throughput and latency requirements of the EMD 20. Many EMDs (e.g., wearable or implanted EMDs) have very limited memory and CPU resources. The PTM 335 ensures that the candidate EMD application communication interface 80 for the EMD 20 does not exceed the memory and CPU profile of the EMD 20 even under maximum operational duress. Many EMDs 20 require that data transfers be achieved quickly and efficiently, and the tests performed by the PTM 335 ensure that the candidate interfaces 80, 85 meet the requisite throughput and latency under high load. The performance tests of the PTM 335 ensure that the performance of each candidate interface 80, 85 is acceptable in a variety of challenging conditions and failure modes.

Each candidate interface is accepted for use in the EMD 20 and the data storage medium 44 only after it successfully passes (337) each of the tests imposed by the ITM 336. In one embodiment, if one or more tests of a candidate interface results in a failure, an error report 338 is provided to the system user/software designer to indicate which tests were failed and why. In some embodiments, suggestions for remediation of the failure(s) may also be provided. If the failures cannot be remedied, the candidate interface must be discarded and a new interface generated. If all tests are passed, the result is an EMD Language Specific Interface (EMD LSI) 350, comprising an EMD application communication interface 80 that may be uploaded (or stored and later uploaded) into the EMD 20, and a central communication interface 85 that may be similarly uploaded into a data storage medium 44.

In one embodiment, each of the FTM 333, STM 334, and PTM 335, which together comprise the ITM 336, generate test reports indicating the performance of the candidate interfaces 80, 85 for each test, in compliance with medical device industry standards for software, such as ISO 13485, IEC 62304, and regulations such as FDA Design Controls and CE Marking. In some embodiments, the reports may also provide guidance or suggestions to remediate any test failures.

Figure 5:
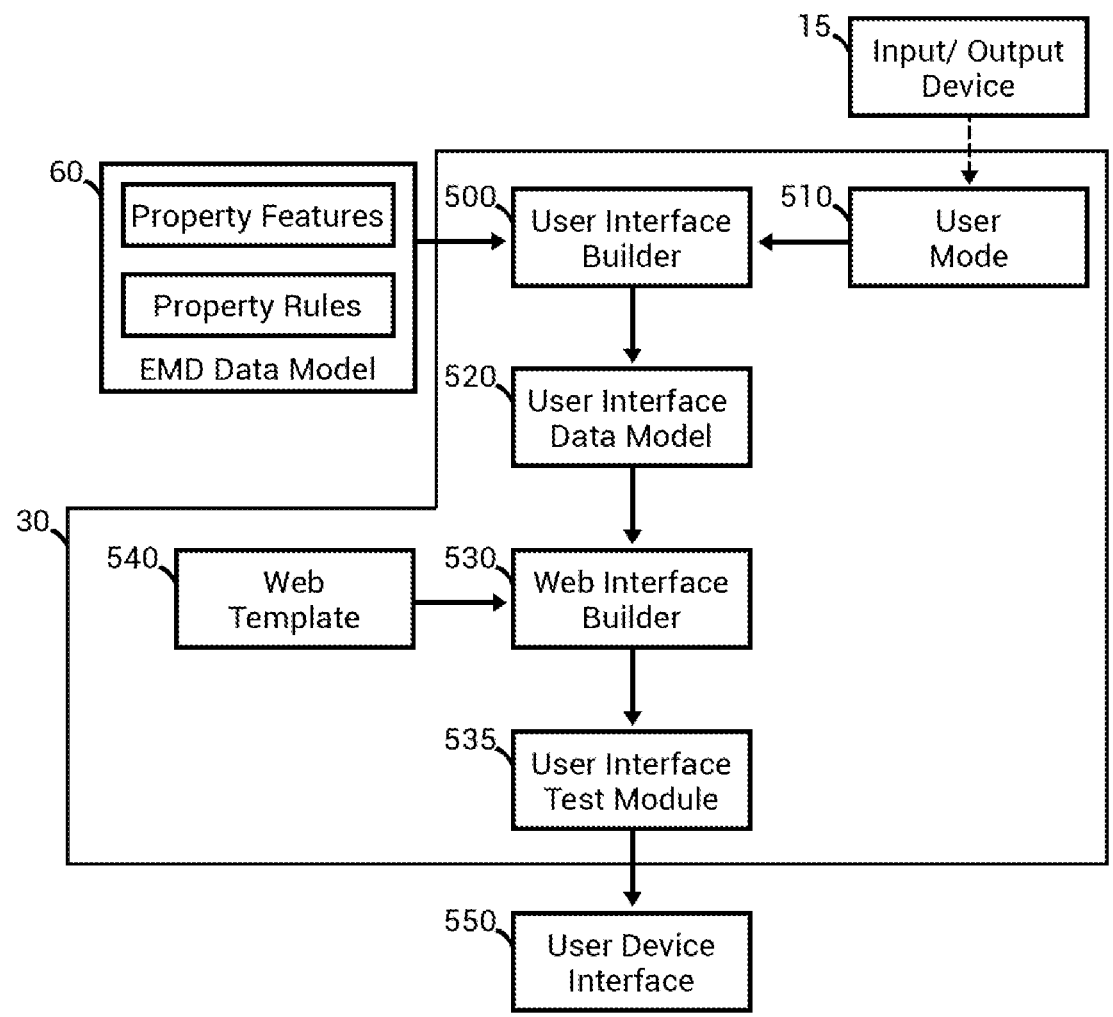
FIG. 5 is a diagram of an embodiment of a User Device Interface Generator module for use in automated generation of medical device software.

FIG. 5 illustrates one embodiment of the EMD User Device Interface Generator (UDIG) module 30 of FIG. 1 to automatically generate one or more software EMD User Device Interfaces (e.g., UDIs 31, 33, 35). Each of the EMD UDIs allows one or more EMD user devices (e.g., a healthcare provided device 32, a patient device 34, an OEM server 36) to access EMD data from a data storage medium 44. The UDIG module 30 uses the property features and rules from the EMD Data Model 60 as inputs. The system user/software developer selects an EMD user mode from an EMD User Mode module 510 (e.g., with an input/output device 15) to identify the type of EMD user (e.g., a healthcare provider), and a User Interface Builder (UIB) module 500 then adapts the EMD property features and rules from the EMD Data Model 60 to generate an EMD User Interface Data Model 520 of the desired interface for the selected EMD user mode. In an alternative embodiment, the system user may select the EMD user mode while defining the EMD property blocks in the Device Modeler 50, such that the EMD user mode is included as part of the EMD Data Model 60.

As noted in the discussion of the EMD Data Model 60 from FIG. 2, the property features and property rules of the EMD Data Model 60 may include rules regarding whether and how a device property is to be available to a particular user (e.g., a patient). The UIB module 500 uses the property features and rules in the EMD Data Model 60, together with the EMD user mode selected by the system user/developer (i.e., a selected user class such as a patient, healthcare provider, etc.) to generate an EMD User Interface Data Model 520 as a high-level data model of the EMD user interface. The EMD User Interface Data Model 520 specifies which EMD data is authorized to be displayed for the particular EMD user class, and the rules governing their display, and is somewhat analogous to the Generic EMD Communication Interface 320 of the EMDIG module 70.

The UDIG module 30 also includes a Web Template file 540, which is a template defining generic elements for how the EMD user interface will be displayed (e.g., colors, text boxes, graphical elements, fonts, etc.) on the EMD user device (e.g., 32, 34, 36). A Web Interface Builder (WIB) module 530 adapts the web template file 540 to reflect the properties and rules in the high-level EMD User Interface Data Model 520 and automatically generates software for a candidate EMD user device interface for a specifically selected EMD user. The candidate EMD user interface reflects the software developer's choices for display of EMD data but is automatically generated in an interface language (e.g., HTML, CSS, or JS) appropriate for the particular type of EMD user device.

The candidate EMD user interface generated by the WIB module 530 is tested by a User Interface Test (UIT) module 535 for a particular type of user device (e.g., healthcare provider device 32). The UIT module 535 performs tests on the candidate user interface for functionality, security and performance similar to the tests performed by Interface Test Module 336 for the EMD application communication interface 80 and the central communication interface 85 that together comprise the EMD LSI 350 (FIG. 3B). In one embodiment, the UIT module 535 tests ensure that the candidate user device interface complies with applicable government and industry standards and regulations for electronic medical devices (e.g., class I, II or III medical devices). These may include, without limitation, ISO 13485, IEC 62304, and regulations such as FDA Design Controls and CE Marking. In one embodiment, the UIT module 535 tests the functionality of the candidate EMD user interface from the WIB module 530 to ensure that the data is displayed properly on the particular user device (e.g., 32, 34, 36), and that user interactions such as filtering, sorting, and data analysis function correctly across different browsers, devices and operating systems. In one embodiment, the UIT module 535 performs security testing to ensure that the data transferred between the user device and the data storage medium 44 is encrypted in transit, that data privacy is enforced so that there is no accidental exposure of protected data, and that no data is stored locally on the user device once the user terminates the user device session. In one embodiment, the UIT module 535 conducts performance tests to verify that acceptably large volumes of data can be handled by the candidate user interface within given latency and throughput limits.

The candidate user interface is accepted as a User Device Interface 550 only after all test performed by the UIT module 535 are passed. In one embodiment, an error report (not shown) may be displayed to the system user for failed tests. The error report may include a description and cause of the failure, as well as suggestions or prompts to enable the failure to be corrected. Depending upon the EMD user selected by the developer in the EMD User Mode module 510, the EMD User Interface 550 is a specific embodiment of a UDI referred to in FIGS. 1A and 1B (e.g., UDI 31 for access by a healthcare provider 32, UDI 33 for use in a patient device, or UDI 35 for an OEM server).

Figure 4:
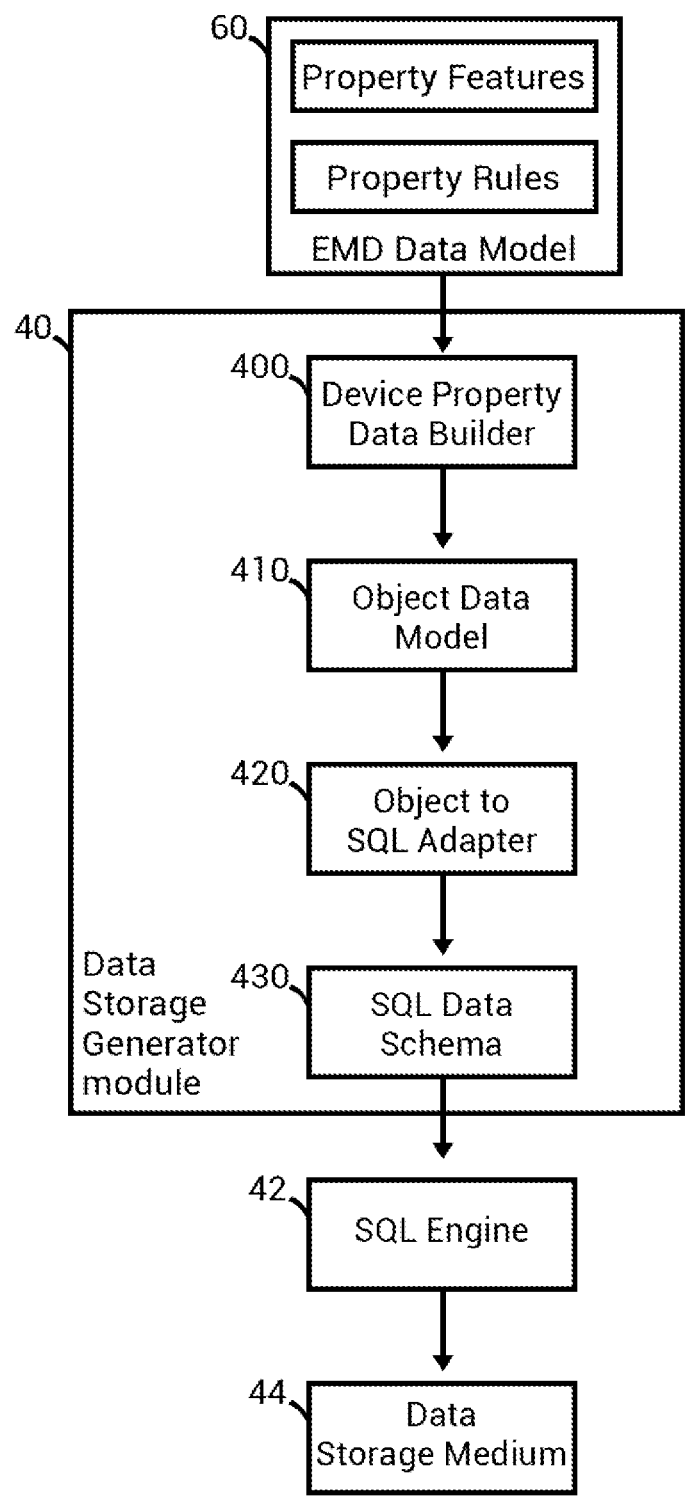
FIG. 4 is a diagram of an embodiment a Data Storage Generator module for use in automated generation of medical device storage software.

FIG. 4 illustrates one embodiment of a Data Storage Generator (DSG) module 40 for automatically generating a SQL data schema for storage of EMG 20 data to a data storage medium 44 using a SQL storage engine 42. The DSG module 40 uses the property features and property rules from the EMD Data Model 60 as inputs to a Device Property Data Builder 400, which uses them to provide an object data model 410 for storage of the data. In one embodiment, the Device Property Data Builder 400 converts the property features and rules of the EMD Data Model 60 from a list format data model to an object format data model 410. The object data model 410, in turn, is converted by an Object to SQL Adapter 420 from an object format to a SQL data schema 430.

As noted in the discussion of FIG. 1, in alternative embodiments (not shown) DSG module 40 may generate data storage schemas according to different storage architectures instead of SQL. These storage architectures may include, without limitation, NoSQL, NewSQL, or other hybrid systems incorporating features of both SQL and NoSQL. Without limitation, in one embodiment the Object to SQL Adapter 420 may be replaced to an Object to NoSQL Adapter (not shown) to convert the object data model 410 from an object format to a NoSQL data schema (not shown).

Referring again to FIG. 4, the SQL data schema 430 (or alternatively a NoSQL data schema) produced by the DSG module 40 is then programmed into an SQL engine 42 (or a NoSQL engine in an alternative embodiment) and used by the SQL engine to store EMD data in the data storage medium 44 as a database. In one embodiment, the EMD data is stored in compliance with one or more of FDA or privacy regulations and statutes. In one embodiment, the SQL data schema automatically generated by DSG module 40 is compliant with class III medical device standards and regulations, while in alternative embodiments, it is compliant with the standards of a selected class (I, II, or III).

Figure 6:
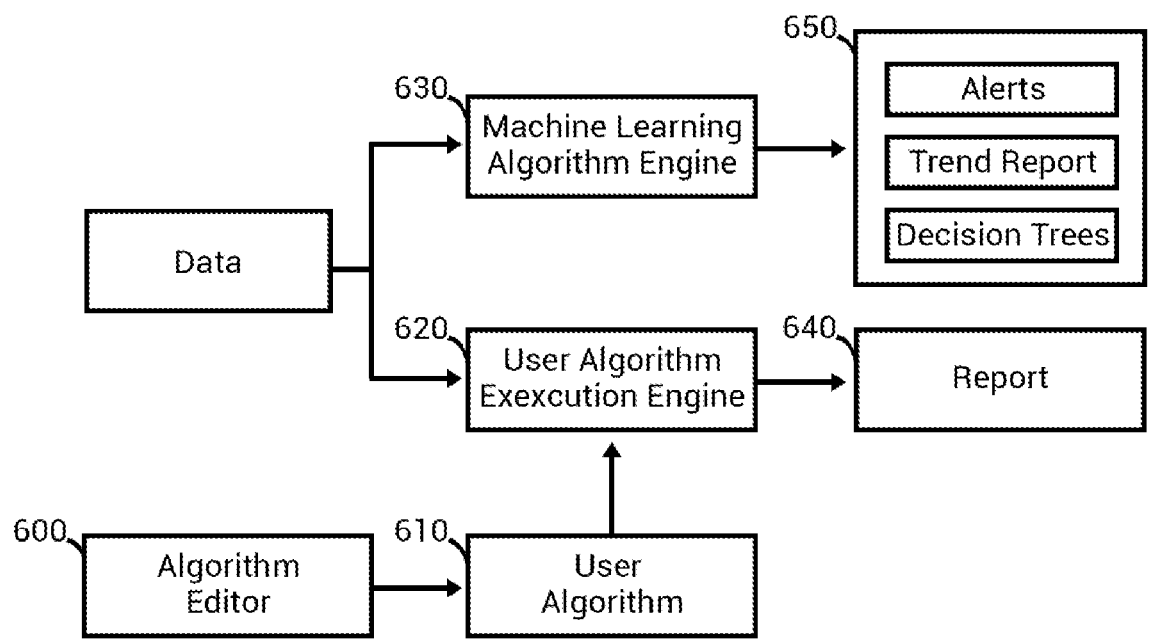
FIG. 6 is a diagram of an embodiment of a module for automated generation of software for analyzing medical device data.

FIG. 6 illustrates one embodiment of an EMD Data Analysis (EMDDA) module 90 (FIG. 1) for automatically generating software for analyzing EMD 20 data. Although FIG. 6 illustrates one embodiment of a module for automatically generating EMD data analysis software, in view of the present disclosure, other embodiments of such a system will be apparent to persons of skill in the art and are within the scope of the present disclosure.

In one embodiment, the EMDDA module 90 includes an Algorithm Editor (AE) 600 accessible by a developer via in input/output device 15 such as a keyboard or workstation. The AE module 600 allows a system user/software developer (e.g., an OEM software engineer) to define an algorithm 610 for execution by a User Algorithm Execution Engine (UAE) module 620. In one embodiment, the UAE module 620 executes the algorithm using data received from an EMD 20 and stored in a data storage medium 44. In one embodiment, the UAE module 620 executes the algorithm using property features and/or property rules from the EMD Data Model 60. In a further embodiment, the UAE module 620 executes the algorithm using both EMD data from the data storage medium 44 and property features and property rules from the EMD Data Model 60. The UAE module 620 generates a User Algorithm Report 940 based on the algorithm output, and the User Algorithm Report 640 may be stored in data storage medium 44 for retrieval by a user device (e.g., healthcare provider device 32) via a User Device Interface for that user (e.g., UDI 31).

In another aspect, the EMDDA module 90 (FIG. 1) may also comprise a Machine Learning Algorithm (MLA) module 630. The MLA module 630 uses machine learning and data mining to analyze data from one or more of EMD 20 data, data stored in the data storage medium 44, and the property features and rules specified in the EMD Data Model 60. The MLA module 630 may include machine learning algorithms to perform a variety of tasks, which may include, without limitation, identifying trends in data, generating alerts that may be forwarded to one or more users automatically, classifying disease states, identify patient status on one or more diagnostic or treatment axes, generate decisions trees, or other analytic tasks that may be performed automatically on data stored in the EMD 20, the data storage medium 44, and/or maintained in the EMD Data Model 60. The MLA module 630 generates one or more Machine Learning Algorithm Reports 650, which may be stored in the data storage medium 44 for retrieval by a user.

In various embodiments, the present disclosure relates to the subject matter of the following numbered paragraphs.

101. A system for automated generation of interface software for data transfer between an electrical medical device (EMD) and a data storage medium, comprising:
a medical device modeler for receiving an input defining one or more EMD properties, the medical device modeler comprising a property validator module to validate each medical device property and providing an EMD data model comprising a set of validated medical device properties and property rules;
an EMD interface generator module for automatically generating, based on the EMD data model,
an EMD communication interface to allow an EMD to transmit data to the system, and
a system interface to receive data transmitted from the EMD.

102. The system of claim 101, further comprising a storage medium for storing data received by the system interface.

103. The system of claim 101, wherein the EMD communication interface and the system interface comply with one or more governmental standards for EMDs set by the United States Food & Drug Administration (USFDA).

104. The system of claim 103, wherein the EMD communication interface and the system interface comply with one or more governmental standards for class III medical devices.

105. The system of claim 103, wherein the EMD communication interface and the system interface comply with one or more standards from a selected medical device class selected from class I medical devices, class II medical devices, and class III medical devices.

106. The system of claim 103, wherein the EMD communication interface and the system interface comply with one or more industry standards selected from ISO 13485, IEC 82304 and ISO 14971.

107. The system of claim 101, wherein the medical device modeler comprises
a property input module for receiving an input defining one or more features for each medical device property, and at least one rule for each said property; and
a property validator module for validating the one or more features and the at least one rule for each medical device property.

108. The system of claim 101, wherein the EMD interface generator module comprises
a device property interface builder for generating a generic EMD communication interface based on the EMD data model; and
an EMD interface language adapter for automatically generating said EMD communication interface and said system interface in a desired interface language based on the generic EMD communication interface.

109. The system of claim 108, wherein the device property interface builder generates the generic EMD communication interface based on the EMD data model and a generic communication template.

110. The system of claim 108, wherein the EMD interface language adaptor generates the EMD communication interface and the system interface by applying programming language-specific rules to the generic EMD communication interface.

111. The system of claim 101 wherein the EMD communication interface is programmed into the EMD as one or more of software and firmware.

112. A system for automated generation of interface software for a user device for obtaining electrical medical device (EMD) data from a storage medium, comprising:

a medical device modeler for receiving an input defining one or more EMD properties, the medical device modeler comprising a property validator module to validate each medical device property and providing an EMD data model comprising a set of validated medical device properties and property rules; and a user device interface generator module for automatically generating, based on the EMD data model, at least one user device interface to allow a user device to access EMD data from a storage medium.

113. The system of claim 112, wherein the user device comprises a device selected from a clinician programmer for an EMD, a patient device to communicate with an EMD coupled to the patient's body, and an OEM server.

114. The system of claim 112, wherein the medical device modeler comprises a property input module for receiving an input defining one or more features for each medical device property, and at least one rule for each said property; and a property validator module for validating the one or more features and the at least one rule for each medical device property.

115. The system of claim 112, wherein the user device interface generator module comprises a user interface builder module for generating a user interface data model based on the EMD data model; and a web interface builder module for automatically generating the user device interface based on the user interface data model and a web template defining generic elements for how the user device interface will be displayed.

116. The system of claim 115, wherein the user interface builder module generates the user interface data model based on the EMD data model and a user mode.

117. The system of claim 116, wherein the user mode identifies a user selected from one of a clinician, a patient, and an original equipment manufacturer.

118. The system of claim 115, wherein the web template defines at least one of colors, text elements, graphical elements, and fonts for the user interface display.

119. The system of claim 115, wherein the web interface builder module automatically generates the user device interface in an interface language selected from HTML, CSS, and JS.

120. The system of claim 112, wherein the user device interface is programmed into the user device as software.

121. A system for automated generation of software for analyzing electrical medical device (EMD) data, comprising:

a storage medium having stored data obtained from an EMD; and a machine learning algorithm module for automatically analyzing stored data from an EMD using machine learning and for generating machine learning algorithm reports, wherein the machine learning algorithm module automatically performs at least one task using the stored data obtained from an EMD, the at least one task selected from identifying trends in the data, generating alerts that may be forwarded to a user, classifying disease states, identifying patient status, generating decision trees, and wherein the machine learning algorithm automatically stores the machine learning algorithm reports in the storage medium.

122. The system of claim 121, further comprising a medical device modeler for receiving an input defining one or more EMD properties, the medical device modeler comprising a property validator module to validate each medical device property and providing an EMD data model comprising a set of validated medical device properties and property rules;

wherein the machine learning algorithm automatically analyzes stored data obtained from an EMD using at least one of the validated medical device properties and property rules from the EMD data model.

123. The system of claim 121, wherein the machine learning algorithm automatically forwards at least one of said reports to a user selected from a clinician, a patient, and an original equipment manufacturer on a periodic basis.

124. A system for automated generation of software for analyzing electrical medical device (EMD) data, comprising:

a storage medium having stored data obtained from an EMD;

an algorithm editor for receiving an input defining an algorithm; and a user algorithm execution module for executing the algorithm using the stored data obtained from an EMD, wherein the user algorithm execution module automatically generates user algorithm reports and stores the algorithm reports in the storage medium.

125. The system of claim 124, further comprising a medical device modeler for receiving an input defining one or more EMD properties, the medical device modeler comprising a property validator module to validate each medical device property and providing an EMD data model comprising a set of validated medical device properties and property rules;

wherein the user algorithm execution module executes the algorithm using at least one of the validated medical device properties and property rules from the EMD data model.

201. A method for automated generation of interface software for data transfer between an electrical medical device (EMD) (20) and a data storage medium (DSM) (44), comprising:

receiving an input defining one or more EMD properties;

testing each EMD property with at least one validation test;

producing an EMD data model (60) comprising a set of validated EMD properties (232, 234) based on said testing; and automatically generating, based on the EMD data model (60):

an EMD application communication interface (80) comprising software in a first desired computer language, wherein said software is capable of allowing an EMD (20) to transmit data to a DSM (44) and receive data transmitted from the DSM (44); and a central communication interface (85) comprising software capable of allowing the DSM (44) to transmit data to the EMD (20) and receive data transmitted from the EMD (20).

202. The method of claim 201 wherein receiving an input defining one or more EMD properties comprises receiving an input defining one or more of data to be stored, data to be transferred, and data to be determined by the EMD (20) or the DSM (44).

203. The method of claim 201 wherein validating each EMD property comprises validating at least one property feature and at least one property rule.

204. The method of claim 201 further comprising embedding the EMD application communication interface (80) in a processor for operation inside the EMD (20).

205. The method of claim 201 further comprising embedding the central communication interface (85) in a processor for operation inside the DSM (44).

206. The method of claim 201 wherein automatically generating the central communication interface (85) comprises automatically generating software in a second desired computer language.

207. The method of claim 206 wherein automatically generating software in a second desired computer language comprises automatically generating software in a computer language different from the first desired computer language.

208. The method of claim 201, wherein testing each EMD property comprises testing each EMD property with at least one of a property rule validation test, a property type validation test, a property attribute validation test, and a property hierarchy validation test.

209. The method of claim 201 wherein testing each EMD property comprises generating an error report indicating each EMD property that cannot be validated.

210. The method of claim 201 further comprising providing a generic communication template, wherein automatically generating an EMD application communication interface (80) and a central communication interface (85) comprises automatically adapting the generic communication template, based on the validated EMD properties (232, 234), to produce a generic EMD communication interface.

211. The method of claim 210 wherein automatically generating an EMD application communication interface (80) and a central communication interface (85) comprises automatically adapting the generic EMD communication interface into software in a desired computer language to produce the EMD application communication interface (80) and the central communication interface (85).

212. The method of claim 211 wherein automatically adapting the generic EMD communication interface into software in a desired computer language comprises automatically converting one or more portions of the generic EMD communication interface into computer language-specific software in a desired computer language.

213. The method of claim 212 wherein automatically adapting the generic EMD communication interface into software in a desired computer language comprises automatically converting one or more portions of the generic EMD communication interface into one of C, C+, C++, C#, and Java software.

214. The method of claim 211 wherein automatically adapting the generic EMD communication interface into software in a desired computer language comprises automatically converting one or more portions of the generic EMD communication interface into a candidate interface for testing.

215. The method of claim 201 wherein automatically generating an EMD application communication interface (80) and a central communication interface (85) comprises testing at least one candidate interface to ensure that the EMD application communication interface (80) and the central communication interface (85) comply with one or more government regulations or industry standards.

216. The system of claim 215 wherein testing at least one candidate interface comprises testing at least one candidate interface to ensure that the EMD application communication interface (80) and the central communication interface (85) comply with at least one of ISO 13485, IEC 82304 and ISO 14971

217. The method of claim 215 wherein testing at least one candidate interface comprises performing at least one of:

a functionality test to ensure that the candidate interface meets the functional requirements for data exchange between the EMD (20) and the DSM (44) specified in the EMD data model (60);

a security test to ensure that
the EMD data cannot be accessed by unauthorized users;
data stored in the EMD (20) and the DSM (44) is encrypted, and
data in transit between the EMD (20) and the DSM (44) is encrypted; and a performance test to ensure that the candidate interface meets the memory, CPU, throughput and latency requirements for data transfer to and from the EMD (20).

218. A method for automated generation of interface software for transfer of data between a user device (32, 34, 36) for an electrical medical device (EMD) (20) and a data storage medium (DSM) (44) in communication with the EMD (20), comprising:

receiving an input defining one or more EMD properties;
testing each EMD property with at least one validation test;
producing an EMD data model (60) comprising a set of validated EMD properties (232, 234) based on the testing; and
automatically generating, based on the EMD data model (60), a user device interface (31, 33, 35) comprising software to allow a user device (32, 34, 36) to receive EMD data transmitted from a DSM (44) and transmit data to the DSM (44) for transmission to the EMD (20).

219. The method of claim 218 further comprising embedding the user device interface (31, 33, 35) in a processor for operation inside the user device (32, 34, 36).

220. The method of claim 218 wherein automatically generating a user device interface (31, 33, 35) comprises automatically generating software for a webpage for display in the user device (32, 34, 36).

221. The method of claim 218 wherein automatically generating a user device interface (31, 33, 35) comprises automatically generating software in a desired computer language selected from HTML, CSS, or JavaScript.

222. The method of claim 218 wherein automatically generating a user device interface (31, 33, 35) comprises automatically generating, based on the validated EMD properties (232, 324) of the EMD data model (60) and a selected user class, a user interface data model (520) specifying which data is authorized to be transmitted to a particular user class.

223. The method of claim 222 wherein automatically generating a user device interface (31, 33, 35) comprises automatically generating, based on a web template file (540) and the user interface data model (520), software for a candidate user device interface for a selected user class.

224. The method of claim 218 wherein automatically generating a user device interface (31, 33, 35) comprises testing at least one candidate user device interface to ensure that the candidate user device interface complies with one or more government regulations or industry standards.

225. The method of claim 224 wherein automatically generating a user device interface (31, 33, 35) comprises performing at least one of a functionality test, a security test, and a performance test on a candidate user device interface.

The particular embodiments disclosed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention. Examples are all intended to be non-limiting. It is therefore evident that the particular embodiments disclosed above may be altered or modified and all such variations are considered within the scope and spirit of the invention, which are limited only by the scope of the claims.

The invention claimed is:

1. A system for automated generation of interface software for data transfer between an electrical medical device (EMD) and at least a first data storage medium (DSM), comprising:
  a first data storage medium (DSM);
  a medical device modeler coupled to at least one input/output device and capable of receiving from a system user using the input/output device an input defining one or more EMD properties, wherein each of the one or more EMD properties 1) comprises at least one property feature and at least one property rule, wherein the at least one property feature is selected from data type, name, size, frequency of upload, or hierarchical relationship with another property, and the at least one property rule is selected from values permitted for the data type, values within a defined range, a type or types of users permitted to access the property, a formula for a calculation to be performed on the property, and consistency of a first parameter or attribute of the property with a second parameter or attribute of the property, and 2) defines one of a) data to be stored by the EMD or the first DSM, b) data to be transferred by the EMD or the first DSM, and c) data to be determined by the EMD or the first DSM, the medical device modeler comprising:
    a property validator module to test each of the one or more EMD properties with at least a first validation test for the at least one property feature and at least a second validation test for the at least one property rule, to produce an EMD data model comprising a set of validated EMD properties, wherein each validated EMD property comprises at least one validated property feature and at least one validated property rule;
  an EMD interface generator (EMDIG) module comprising:
    an EMD interface language adapter (ILA) module that automatically generates, based on the set of validated EMD properties:
      code for an EMD application communication interface comprising software configured for operating in the EMD in a first desired computer language to allow the EMD to transmit data to the first DSM and to receive data transmitted from the first DSM; and
      code for a central communication interface comprising software to allow the first DSM to transmit data to the EMD and to receive data transmitted from the EMD, and
    a compiler for compiling the code for the EMD application communication interface into an EMD application communication interface program and compiling the code for the central communication interface into a central communication interface program; and
  at least one processor, wherein the medical device modeler and the EMD interface generator module each comprise software executed by the at least one processor.

2. The system of claim 1 wherein at least one of the one or more EMD properties defines data to be transferred by the EMD to the first DSM.

3. The system of claim 1 wherein the central communication interface comprises software configured for operating inside the first DSM.

4. The system of claim 1 wherein the central communication interface comprises software in a second desired computer language different from the first desired computer language.

5. The system of claim 1, wherein the property validator module comprises:
  at least one of a property type validator module, a property attribute validator module, and a property hierarchy validator module to test the at least one property feature with the at least a first validation test; and
  a property rule validator module to test the at least one property rule with the at least a second validation test.

6. The system of claim 1 wherein the medical device modeler further comprises:
  an error report generator for providing feedback for each EMD property that cannot be validated.

7. The system of claim 1 wherein the EMD interface generator module further comprises:
  a generic communication template and a device property interface builder (DPIB) module, where the device property interface builder module automatically adapts the generic communication template, based on the validated EMD properties, to produce a generic EMD communication interface.

8. The system of claim 7 wherein the EMD interface language adapter module automatically adapts the generic EMD communication interface into software in a desired computer language to produce an EMD language specific interface comprising the EMD application communication interface in the first desired computer language, and the central communication interface.

9. The system of claim 8 wherein the EMD interface language adapter module comprises:
  a substitution generator module for automatically converting one or more portions of the generic EMD communication interface into computer language-specific software in the first desired computer language to produce the EMD application communication interface in the first desired computer language.

10. The system of claim 9 wherein the desired computer language is selected from C, C++, C#, and Java.

11. The system of claim 8 wherein the EMD interface language adapter module comprises:
  a substitution generator module for automatically converting one or more portions of the generic EMD communication interface into a candidate interface in the first desired computer language for testing by an interface test module.

12. The system of claim 1 wherein the EMD interface language adapter module comprises:
  an interface test module (ITM) to test at least one candidate interface to ensure that the EMD application communication interface complies with one or more government regulations or industry standards.

13. The system of claim 12 wherein the one or more government regulations or industry standards comprises at least one of ISO 13485, IEC 82304 and ISO 14971.

14. The system of claim 1 wherein the EMD interface language adapter module comprises:
an interface test module comprising at least one of:
(1) a functionality test module to test at least one candidate interface to ensure that the candidate interface meets the functional requirements for data exchange between the EMD and the DSM specified in the EMD data model;
(2) a security test module to test the at least one candidate interface to ensure that
(a) the EMD data cannot be accessed by unauthorized users;
(b) data stored in the EMD and the DSM is encrypted, and
(c) data in transit between the EMD and the DSM is encrypted; and
(3) a performance test module to ensure that the candidate interface meets the memory, CPU, throughput and latency requirements for data transfer to and from the EMD.

15. A system for automated generation of interface software for transfer of data between a user device for an electrical medical device (EMD) and at least a first data storage medium (DSM) in communication with the EMD, comprising:
a first data storage medium (DSM);
a medical device modeler coupled to at least one input/output device and capable of receiving from a system user using the input/output device an input defining one or more EMD properties, wherein each of the one or more EMD properties 1) comprises at least one property feature, wherein the at least one property feature is selected from data type, name, size, frequency of upload, or hierarchical relationship with another property, and at least one property rule comprising at least one access rule indicating at least one type of user who may access the EMD property, and 2) defines one of a) data to be stored by the EMD, the first DSM, or a user device, and b) data to be transferred by the EMD, the first DSM, or the user device, the medical device modeler comprising:
a property validator module to test each of the one or more EMD properties with at least a first validation test for the at least one property feature and at least a second validation test comprising at least one access rule validation test for the at least one property rule, wherein the property validator module produces an EMD data model comprising a set of validated EMD properties, wherein each validated EMD property comprises at least one validated property feature and at least one validated property rule including at least one validated access rule;
an EMD interface generator (EMDIG) module comprising an EMD interface language adapter (ILA) module that automatically generates, based on the set of validated EMD properties, code for a central communication interface comprising software to allow the first DSM to transmit data to the user device and to receive data transmitted from the user device;
a user device interface generator (UDIG) module comprising an EMD user mode module that identifies a type of EMD user, wherein the UDIG module automatically generates, based on the set of validated EMD properties and the identified type of EMD user, code for a user device interface (UDI) comprising software configured for operating in the user device to allow the user device to receive EMD data transmitted from the first DSM and to transmit data to the first DSM for transmission from the first DSM to the EMD;
a compiler for compiling the code for the UDI into a UDI program and compiling the code for the central communication interface into a central communication interface program;
and
at least one processor, wherein the medical device modeler, the EMD interface generator module, and the user device interface generator module each comprise software executed by the at least one processor.

16. The system of claim 15 wherein the user device interface comprises software for a webpage for display in the user device.

17. The system of claim 15 wherein the user device interface comprises software in a desired computer language selected from HTML, CSS, or JavaScript.

18. The system of claim 15 wherein the user device interface generator module further comprises:
a user interface builder (UIB) module to automatically generate, based on the set of validated EMD properties and the identified type of EMD user, a user interface data model of the user device interface that specifies which data is authorized to be transmitted to a particular type of EMD user.

19. The system of claim 18 wherein the user device interface generator module generates a candidate user device interface, the user device interface generator module further comprising:
a web interface builder module to automatically generate, based on a web template file and the user interface data model, a candidate user device interface for a selected type of EMD user.

20. The system of claim 15 wherein the user device interface generator module generates a candidate user device interface, the user device interface generator module further comprising:
a user interface test (UIT) module to test the candidate user device interface to ensure that the candidate user device interface complies with one or more government regulations or industry standards.

21. The system of claim 15 wherein the user device interface generator module generates a candidate user device interface, the user device interface generator module further comprising:
a user interface test (UIT) module to perform at least one of functionality tests, security tests, and performance tests on the candidate user device interface.

22. The system of claim 1, wherein the central communication interface comprises software to allow a cloud-based first DSM to transmit data to the EMD and to receive data transmitted from the EMD to the cloud-based first DSM.

23. A system for automated generation of interface software for data transfer between an electrical medical device (EMD) and a user device for the EMD using a first data storage medium (DSM), comprising:
a first data storage medium (DSM);
a medical device modeler coupled to at least one input/output device and capable of receiving from a system user using the input/output device an input defining one or more EMD properties, wherein each of the one or more EMD properties 1) comprises at least one property feature, wherein the at least one property feature is selected from data type, name, size, frequency of upload, or hierarchical relationship with another property, and at least one property rule comprising at least one access rule indicating at least one type of user who may access the EMD property, and 2) defines one of a) data to be stored by the EMD, the first DSM, or a user device, b) data to be transferred by the EMD, the first DSM, or the user device, and c) data to be determined by the EMD, the first DSM, or the user device, the medical device modeler comprising:

a property validator module to test each of the one or more EMD properties with at least a first validation test for the at least one property feature and at least a second validation test comprising at least one access rule validation test for the at least one access rule, wherein the property validator module produces an EMD data model comprising a set of validated EMD properties, wherein each validated EMD property comprises at least one validated property feature and at least one validated property rule including at least one validated access rule;

an EMD interface generator (EMDIG) module comprising:

an EMD interface language adapter (ILA) module that automatically generates, based on the set of validated EMD properties:

code for an EMD application communication interface comprising software configured for operating in the EMD in a first desired computer language to allow the EMD to transmit data to the first DSM and to receive data transmitted from the first DSM; and code for a central communication interface comprising software to allow the first DSM to transmit data to the EMD and the user device and to receive data transmitted from the EMD and the user device;

a user device interface generator (UDIG) module comprising an EMD user mode module that identifies a type of EMD user, wherein the UDIG module automatically generates, based on the set of validated EMD properties and the identified type of EMD user, code for a user device interface (UDI) comprising software configured for operating in the user device to allow the user device to receive EMD data transmitted from the first DSM and to transmit data to the first DSM for transmission from the first DSM to the EMD;

a compiler for compiling the code for the EMD application communication interface into an EMD application communication interface program, compiling the code for the central communication interface into a central communication interface program, and compiling the code for the UDI into a UDI program; and at least one processor, wherein the medical device modeler, the EMD interface generator module, and the user device interface generator module each comprise software executed by the at least one processor.

24. The system of claim 1, wherein the at least one property feature includes at least one of a property data type and a property hierarchy, and the at least one property rule includes at least one of a validation rule, an access rule indicating at least one type of user who can access the data, and a calculation rule for calculating the property.

25. The system of claim 1, wherein the medical device modeler is coupled to at least one input/output device selected from a computer keyboard, a computer terminal, and a workstation.

* * * * *